(12) United States Patent
Yaroslavsky et al.

(10) Patent No.: US 11,219,370 B2
(45) Date of Patent: Jan. 11, 2022

(54) DEVICES AND METHODS FOR OPTICAL PATHOLOGY

(71) Applicant: UNIVERSITY OF MASSACHUSETTS, Boston, MA (US)

(72) Inventors: Anna N. Yaroslavsky, North Andover, MA (US); Rakesh Patel, Sharon, MA (US); Dennis Wirth, Wilmington, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 15/838,163

(22) Filed: Dec. 11, 2017

(65) Prior Publication Data
US 2018/0206727 A1 Jul. 26, 2018

Related U.S. Application Data

(63) Continuation of application No. 14/000,106, filed as application No. PCT/US2012/025678 on Feb. 17, 2012, now abandoned.

(Continued)

(51) Int. Cl.
*A61B 5/00* (2006.01)
*G06T 7/00* (2017.01)
(Continued)

(52) U.S. Cl.
CPC .......... *A61B 5/0071* (2013.01); *A61B 5/0068* (2013.01); *A61B 5/0091* (2013.01);
(Continued)

(58) Field of Classification Search
CPC ......... A61B 6/481; A61B 6/52; A61B 6/4887; A61B 6/4836; A61B 5/0059;
(Continued)

(56) References Cited

U.S. PATENT DOCUMENTS 5,127,730 A 7/1992 Brelje
5,995,645 A 11/1999 Soenksen et al.
(Continued)

OTHER PUBLICATIONS

Matsumoto, Brian. Cell biological applications of confocal microscopy. vol. 70. Elsevier, 2003.*
(Continued)

*Primary Examiner* — Carolyn A Pehlke
(74) *Attorney, Agent, or Firm* — Brake Hughes Bellermann LLP

(57) ABSTRACT

Currently most cancers, including breast cancers, are removed without any intraoperative margin control. Postoperative methods inspect 1-2% of the surgical margin and are prone to sampling errors. The present invention relates to an optical imaging system that will enable evaluation of the surgical margin in vivo and in real-time. The invention provides for simultaneous fluorescence and fluorescence polarization imaging. The contrast of the acquired images will be enhanced using fluorescent agents approved for diagnostic use in patients. As the staining pattern of fluorescence images is similar to that of histology, and the values of fluorescence polarization are significantly higher in cancerous as compared to normal cells, the invention provides (Continued)

for further improvements in diagnostic methods. The systems and methods can be applied to the intra-operative delineation of cancerous tissue.

13 Claims, 23 Drawing Sheets

Related U.S. Application Data

(60) Provisional application No. 61/443,931, filed on Feb. 17, 2011.

(51) Int. Cl.
*A61M 5/00* (2006.01)
*A61M 31/00* (2006.01)
*G06T 7/90* (2017.01)

(52) U.S. Cl.
CPC .............. *A61B 5/742* (2013.01); *A61M 5/007* (2013.01); *A61M 31/005* (2013.01); *G06T 7/0012* (2013.01); *G06T 7/90* (2017.01); *G06T 2207/10064* (2013.01); *G06T 2207/10152* (2013.01); *G06T 2207/20221* (2013.01); *G06T 2207/30096* (2013.01)

(58) Field of Classification Search
CPC ...... A61B 5/0084; A61K 49/00; G02B 21/06; G02B 21/0004; G02B 21/24; G01N 21/6428; G01N 21/718; G02F 1/31; G01J 3/42
See application file for complete search history.

(56) References Cited

U.S. PATENT DOCUMENTS

| | | |
|---|---|---|
| 6,233,480 B1 | 5/2001 | Hochman et al. |
| 2003/0236458 A1 | 12/2003 | Hochman |
| 2004/0133112 A1 | 7/2004 | Rajadhyaksha |
| 2004/0249274 A1 | 12/2004 | Yaroslavsky et al. |
| 2005/0094147 A1* | 5/2005 | Yaroslavsky ........ A61B 5/0059 356/417 |
| 2008/0024860 A1* | 1/2008 | Yaroslavsky ........ A61B 5/0068 359/372 |
| 2009/0046360 A1 | 2/2009 | Funk et al. |
| 2009/0080600 A1 | 3/2009 | Keller et al. |
| 2010/0053607 A1 | 3/2010 | Yaroslaysky et al. |

OTHER PUBLICATIONS

"What is Histology" (https://www.histology.leeds.ac.uk/what-is-histology/H_and_E.php; retrieved Dec. 5, 2020).*
Bedard, Noah, et al. "Emerging roles for multimodal optical imaging in early cancer detection: a global challenge." Technology in cancer research & treatment 9.2 (2010): 211-217.
Barbosa, Pedro, and T. Michael Peters. "The effects of vital dyes on living organisms with special reference to methylene blue and neutral red." The Histochemical Journal 3.1 (1971): 71-93.
Pierce, Mark C., David J. Javier, and Rebecca Richards-Kortum. "Optical contrast agents and imaging systems for detection and diagnosis of cancer." International Journal of Cancer 123.9 (2008): 1979-1990.
PCT/US2012/025678, International Search Report dated Oct. 18, 2012.

* cited by examiner

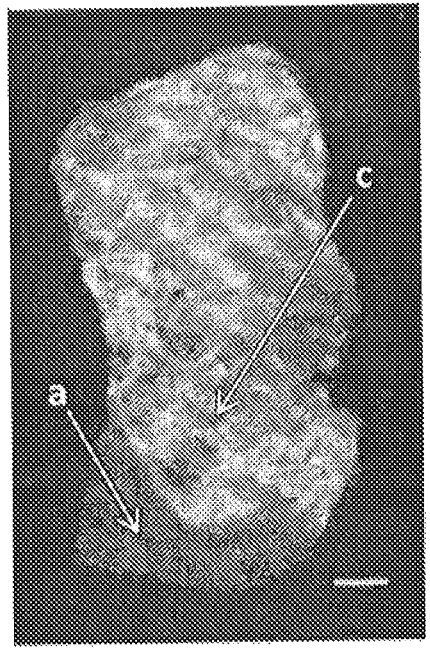 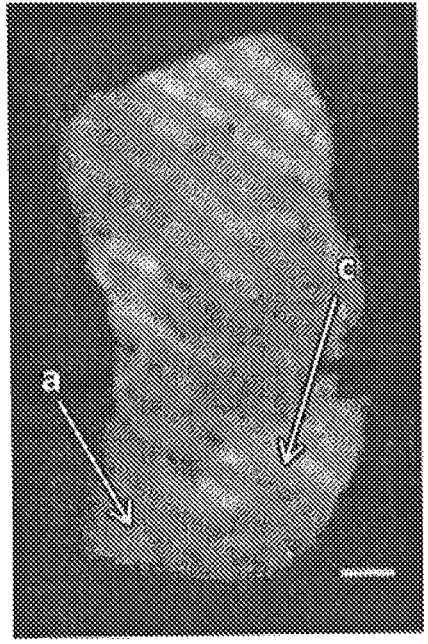
FIG. 8A  FIG. 8B
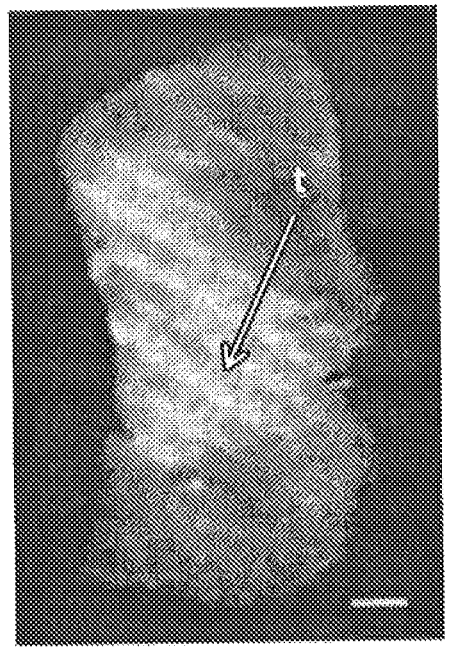 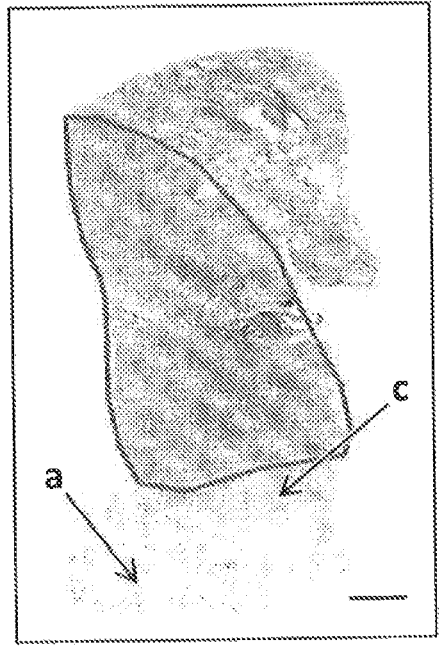
FIG. 8C  FIG. 8D

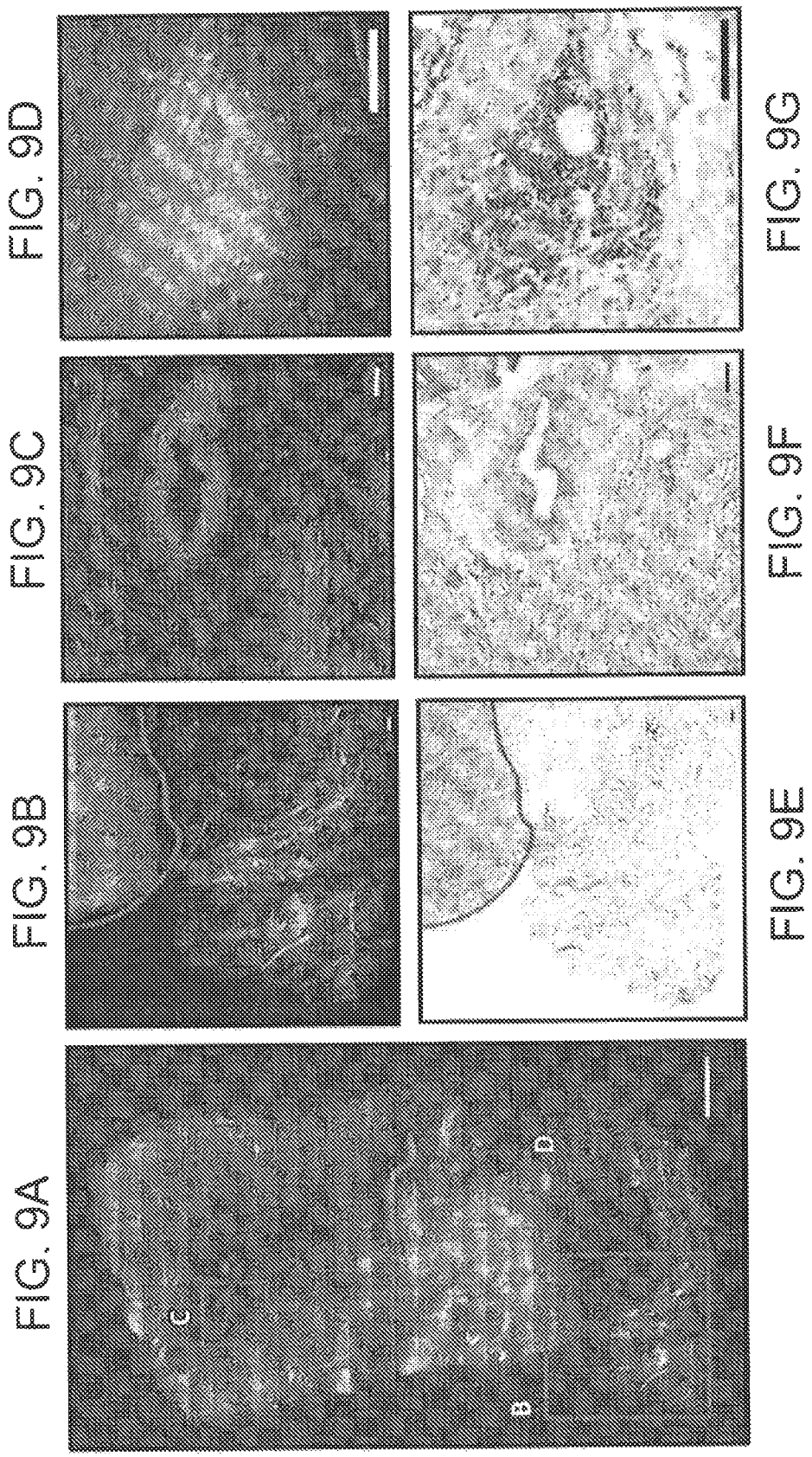

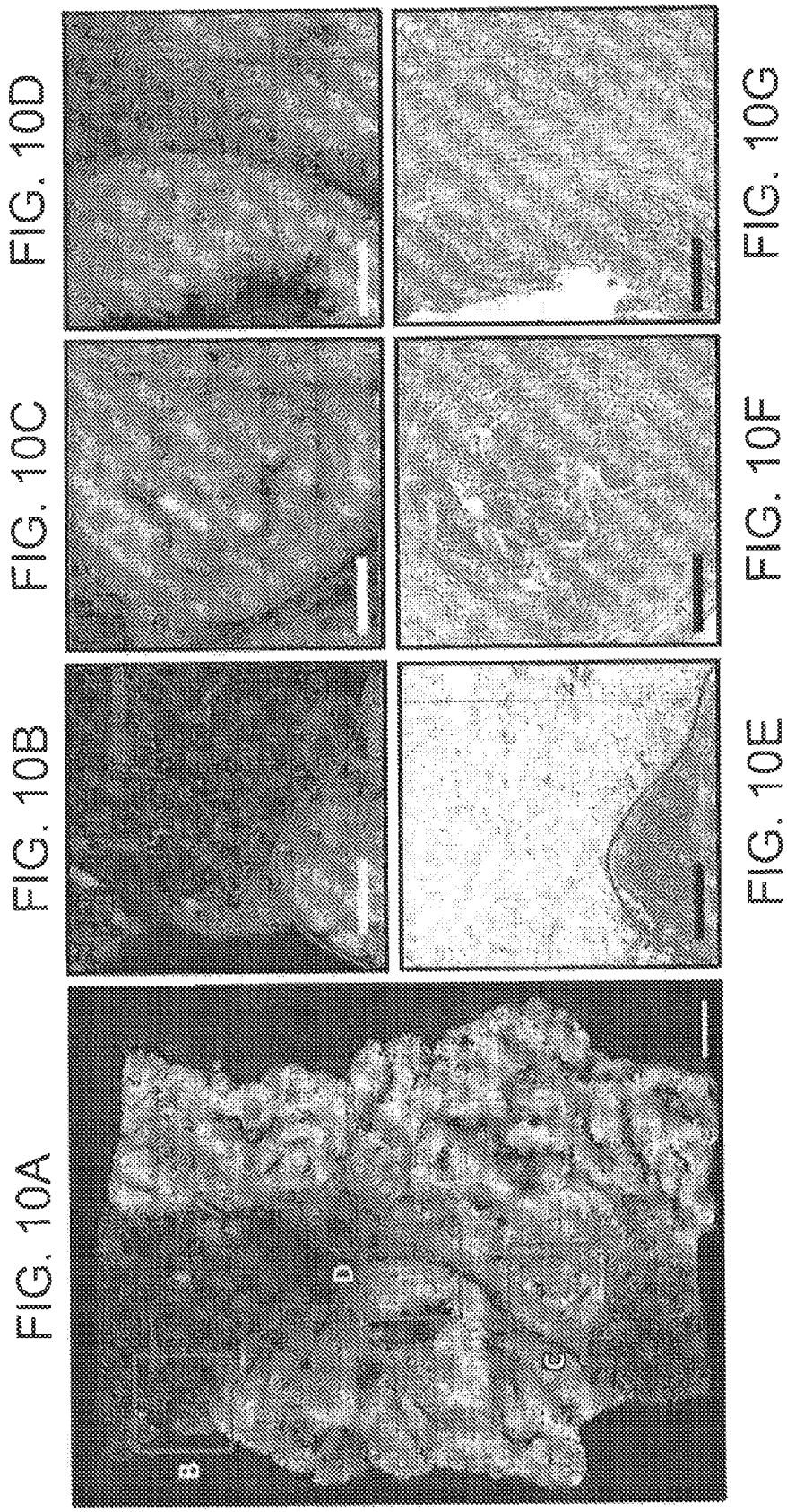

DEVICES AND METHODS FOR OPTICAL PATHOLOGY

CROSS REFERENCE TO RELATED APPLICATIONS

This application is a divisional of U.S. application Ser. No. 14/000,106, filed Aug. 16, 2013, which is a U.S. Application National Stage filed under 31 USC 371 of International Application No. PCT/US2012/025678, filed Feb. 17, 2012, which claims the benefit of U.S. Provisional Application No. 61/443,931, filed Feb. 17, 2011, the entire contents of the above application is incorporated herein by reference.

BACKGROUND OF THE INVENTION

There currently exists no intraoperative in situ methods for detecting and delineating pathology. Currently, in the majority of cases, except for the visual assessment of where to excise, cancers are removed without intraoperative margin control. After the surgery is completed and the resulting wound is closed, the tissue is sent for histopathological analysis. Postoperative methods of cancer delineation involve sampling and examine only 1-2% of the surgical margin. For example, the "bread loaf" method uses vertical sectioning of the excised tissue and is prone to sampling errors, which may lead to cancer recurrence and metastases. If cancerous cells are detected in the pathology slides, the patient has to be brought back to the surgical suite, the wound has to be reopened and more tissue has to be excised. This repetitive procedure doubles the cost of the treatment and involves psychological stress to the patient.

For example, in the case of nonmelanoma skin cancers, Mohs micrographic surgery is used for the removal of tumors. Mohs surgery is a clinical technique that allows complete control of excision margins during the operation. Mohs surgery has a success rate of 95%, but is used in a minority of cases, as it is expensive, tedious, and time-consuming. It requires a pathology laboratory adjacent to the operation room and a technician to prepare the sections.

Thus, there is a need to improve systems and methods for interoperative assessment of cancerous tissue.

SUMMARY OF THE INVENTION

Preferred embodiments of the present invention relate to methods and devices for intraoperative detection of pathological cells and margins. A preferred embodiment uses at least one biological marker or agent that spectrally enhances a tissue component being measured, a plurality of dyes or stains that are delivered to a region of tissue of a patient undergoing surgery for the removal of tissue, such as cancerous tissue. An optical system is used to image the region of tissue for analysis.

Currently, the standard of care for diagnosing almost any type of pathology requires processing using hematoxylin & eosin histopathology (H&E), which involves excising and freezing suspicious tissue, cutting it in thin, 5 µm slices, placing these thin pieces on the slides, multistage staining, and cover slipping these slides. Then the slides are inspected and analyzed under a microscope by a certified pathologist. Hematoxylin is a basic dye and shows up in the acidic part of the cell like the nucleus, where nucleic acids (DNA and RNA) are concentrated. Therefore, hematoxylin is used to demonstrate nuclear and cytoplasmic structures. Eosin is used as a counterstain to hematoxylin. Eosin is an acidic dye and shows up in the basic parts of the cell, i.e. the cytoplasm. Eosin usually appears pink in color to highlight connective tissue and also stains collagen, muscle tissue and red blood cells. Hematoxylin is toxic and cannot be applied in vivo, whereas eosin is approved for human use.

Preferred embodiments of the present invention utilize the similarities of the staining patterns of hematoxylin and certain other stains, such as tetracycline (TCN), methylene blue (MB), and/or toluidine blue (TB) which appear blue in color in contrast to the pink of eosin. Tetracycline and methylene blue are approved for human use in the United States. Toluidine blue is approved for human use in Canada. Therefore, these chromophores/fluorophores can be applied in vivo. The present invention utilizes an acidic stain, such as eosin as an in vivo counterstain to TCN, MB, and/or TB. However, any other dye that stains cytoplasm and is safe for human use can be utilized.

The above mentioned dyes/fluorophores may be introduced into the human body topically (paint/spray application or injection), systemically, such as by oral administration with pills prior to surgery, or intravenously, depending on the body site, type of pathology, and medical procedure. After sufficient amount of dye is accumulated in the tissue of interest, fluorescence and/or fluorescence polarization data can be recorded using optical detection that emulates histological evaluation of the tissue.

To achieve spatial resolution comparable to that of histopathology, a confocal (or multiphoton) imaging system can be used. To achieve wide-field imaging a detector, such as a CMOS-imaging device or CCD-camera, combined with 4-way image splitter can be employed. Nonlinear (two photon) fluorescence can also be used to obtain optical sections of tissue in accordance with the invention.

Fluorescence of the dyes highlighting nuclear structures and cytoplasm is excited by the linearly polarized lasers (or other light sources), respectively. The light is coupled into the system by a dichroic mirror. The imaged point of the confocal image is scanned in x and y directions using a polygon mirror and galvanometric mirror, respectively, or other optical beam scanner. The returning emitted fluorescence light of the longer (or shorter) wavelength is deflected by a dichroic mirror, whereas the fluorescence light of the shorter (or longer) wavelength is deflected by a second dichroic mirror. The light in each fluorescence emission channel is then split into two polarizations (co- and cross-polarized with respect to the incident laser light) using polarizing beam splitters, and registered by photomultiplier tubes (PMTs).

This system enables simultaneous registration of fluorescence and fluorescence polarization images acquired by two different contrast agents. Macroscopic images are registered by the CCD-camera equipped with four-way image splitter. The image splitter has four linearly polarizing filters (one in each channel). Two of the filters are oriented to transmit only the light co-polarized with the light incident on the sample, the other two are oriented to transmit only the light cross-polarized with respect to the incident light. Each channel of the splitter also contains bandpass filters (two bandpass filters to transmit fluorescence from the nucleus and two filters for the cytoplasmic stain). This configuration enables simultaneous acquisition of co- and cross-polarized fluorescence for both stains. Light can be delivered and/or collected endoscopically using an endoscope or alternatively, with a hand-held fiber optic probe.

Upon completing image acquisition, fluorescence of the nuclei and cytoplasm stains is color-coded and presented in the same image (either macro-, high-resolution, or both).

Fluorescence polarization images are also displayed: nucleus stain to indicate possible locations of cancer lobules, cytoplasmic stain to indicate alterations of collagen, muscle tissue and cytoplasm.

As the resulting staining pattern mimics that of the conventional H&E histology, the system enables a certified pathologist to interpret and analyze the resulting fluorescence images. Another preferred embodiment can utilize a combination of endogenous chromophores and/or fluorophores (such as collagen) or endogenous fluorophores in combination with one or more applied stains. The systems and methods can be used in the diagnosis and treatment of cancers occurring in the human or animal body including brain, breast, liver, skin, the gastrointestinal system, etc. The system can also be used in the analysis of removed or biopsied tissue samples obtained, for example, by stereotactic needle biopsy.

Preferred embodiments of the invention include combining dye-enhanced macroscopic polarization imaging with multimodal confocal microscopy for intraoperative delineation of breast cancers. Wide-field polarization imaging allows for a rapid macroscopic overview of the entire surface area of the tissue region or specimen, whereas confocal microscopy enables high-resolution imaging with a small field of view. Two major types of breast cancers, including ductal and lobular carcinomas have been measured and analyzed. Wide-field and high-resolution images of recently excised thick breast cancer tissue stained with methylene blue (MB) were acquired. MB fluorescence polarization signals from cancerous and residual normal tissue structures were quantified and compared. Polarization macro-imaging and confocal microscopy to grossly delineate tumor margins and analyze cellular morphology, respectively, was evaluated by comparison with the H&E histopathology.

Reflectance and fluorescence images can be processed to form combined or pseudo color images to provide enhanced discrimination of cancerous tissue. The system has a resolution sufficient to provide for the detection of abnormal tissue at the cellular level. Thus individual cells within a subregion of tissue can be quantatively characterized as normal or abnormal using the fluorescence polarization methods described herein. Fluorescence polarization images of tumor cells were obtained and quantitative values computed on a numeric scale that distinguished between cancerous and normal tissue. Autofluorescence images can also be obtained to further assist in diagnosis of certain conditions.

BRIEF DESCRIPTION OF THE DRAWINGS

FIGS. 8A-8D are wide-field optical and histopathology images of a representative sample with invasive lobular carcinoma; t: tumor; c: connective tissue; a: adipose tissue; scale bar: 1 mm.

FIGS. 9A-9G are images of invasive lobular carcinoma.

FIGS. 10A-10G are images of invasive ductal carcinoma.

DETAILED DESCRIPTION OF THE INVENTION

A method and device for intraoperative, in vivo, detection of pathological cells and margins. Preferred embodiments utilize a plurality of complementing stains that are imaged for delineating cancers such as skin or breast cancers during surgery.

Clinical evidence shows that eligible patients undergoing breast conservation therapy (BCT) have the same long-term survival rate as those undergoing mastectomy, when patients with BCT do not have a local regional recurrence. Thus, complete removal of breast cancer is of primary importance. Currently, re-excision is required in up to 60% cases because most of BCT procedures are performed without intraoperative margin control. Standard histopathological evaluation of the excision margins performed during the surgery reduces re-excision rate to approximately 20%. However, due to high cost, it has not become widely available. Therefore, a reliable cost-effective method for real-time examination of breast cancer margins and other cancers employing surgical removal can be indispensable for surgical oncology.

Two FDA-approved fluorescent agents, TCN and EY, can be used to enhance contrast of cells and connective tissue, respectively. Since 1957, when Rall et al. had noted fluorescence in breast tumors following tetracycline therapy, multiple clinical trials have been conducted that utilized this phenomenon as an aid to diagnostics of the different tumor types. The present invention utilizes the staining pattern of TCN in fluorescence polarization images that is similar to that of hematoxylin. Similarly, EY is an accepted histological stain (Hematoxylin & Eosin Y or "H&E") that is used as a counter-stain, complimentary to hematoxylin. Thus, in vivo tissue staining with TCN and EY, followed by optical inspection of the suspicious tissue using optical imaging, may enable in situ detection of tumor margins and single cancer cells. As the appearance of tissue structures in the images is substantially similar to that in H&E histopathology, this procedure can be readily utilized by a certified pathologist.

Figure 1A:
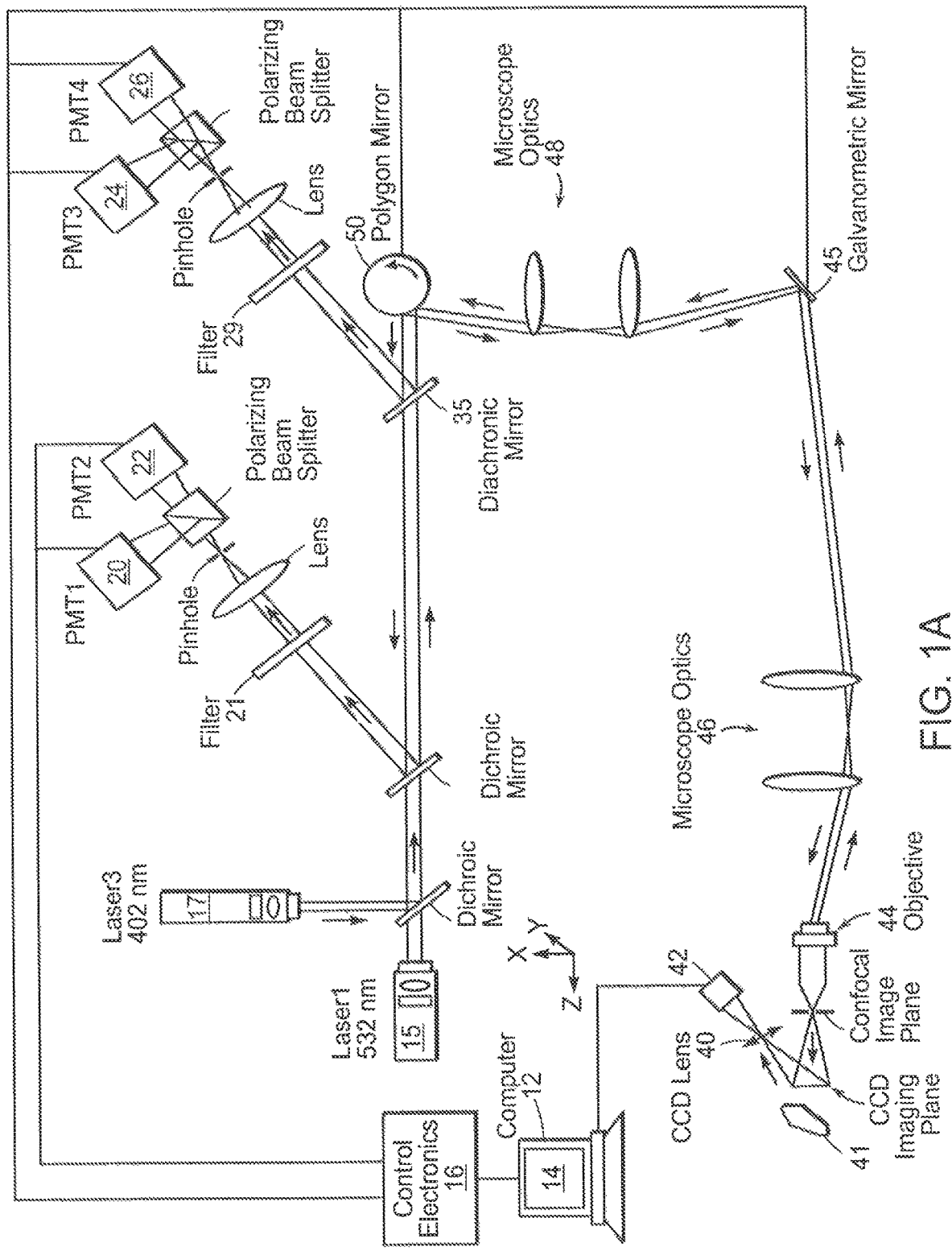
FIG. 1A illustrates a system for histological examination of a patient during surgery.

A wide-field high-resolution system configured for imaging reflectance and fluorescence of the samples stained with tetracycline (TCN) can be used to accommodate TCN and eosin Y (EY) as contrast agents by replacing the reflectance channel with a second fluorescence channel. An illustration of the modified system 10 is presented in FIG. 1A. Two light sources such as a first laser 15 emitting, for example, in the violet portion of the spectrum (e.g. a GaN diode laser emitting at 402 nm) and a second laser 17 emitting, for example, in a green portion of the spectrum (e.g. 532 nm), can be optically coupled through a first scanner 50 (e.g. a polygonal mirror), through a first microscope lens assembly 48, reflected off a second scanner 45, such as a galvanometric mirror, directed through a second microscope lens assembly 46 onto an objective lens 44 for confocal imaging of a region of interest 41 in the tissue of a mammalian subject. A lens 40 is used to image onto a wide field camera 42, while light from the imaging plane within the tissue is returned through the optical system for detection by photomultiplier tube detectors 20, and 24, 26. Filters 21 and 29 are selected based on the emission spectrums of the stains in use. Dichroic mirrors 3 and 35 can be paired with filters 21, 29 to transmit the excitation wavelengths of the lasers and reflect the selected emission bands of TCN and EY, for example.

Figure 1B:
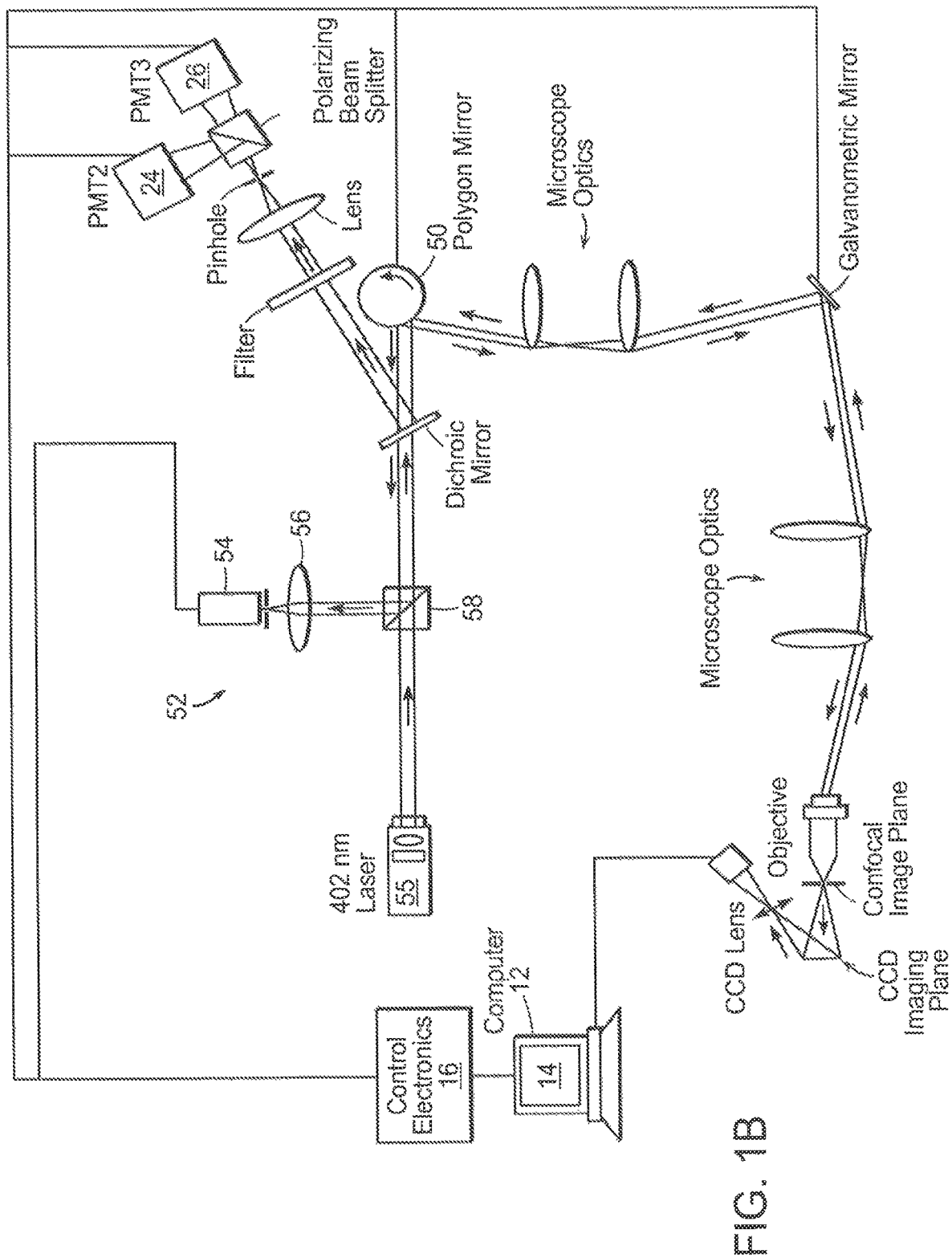
FIG. 1B illustrates a system using a combination of reflectance and fluorescence.

FIG. 1B shows a system employing a confocal reflectance channel 52 in combination with the aforementioned fluorescence polarization channel. In this embodiment a beam splitter 58 directs the reflected signal including the wavelength band from light source 55 through lens 56 to reflectance channel detector 54.

Figure 2A:
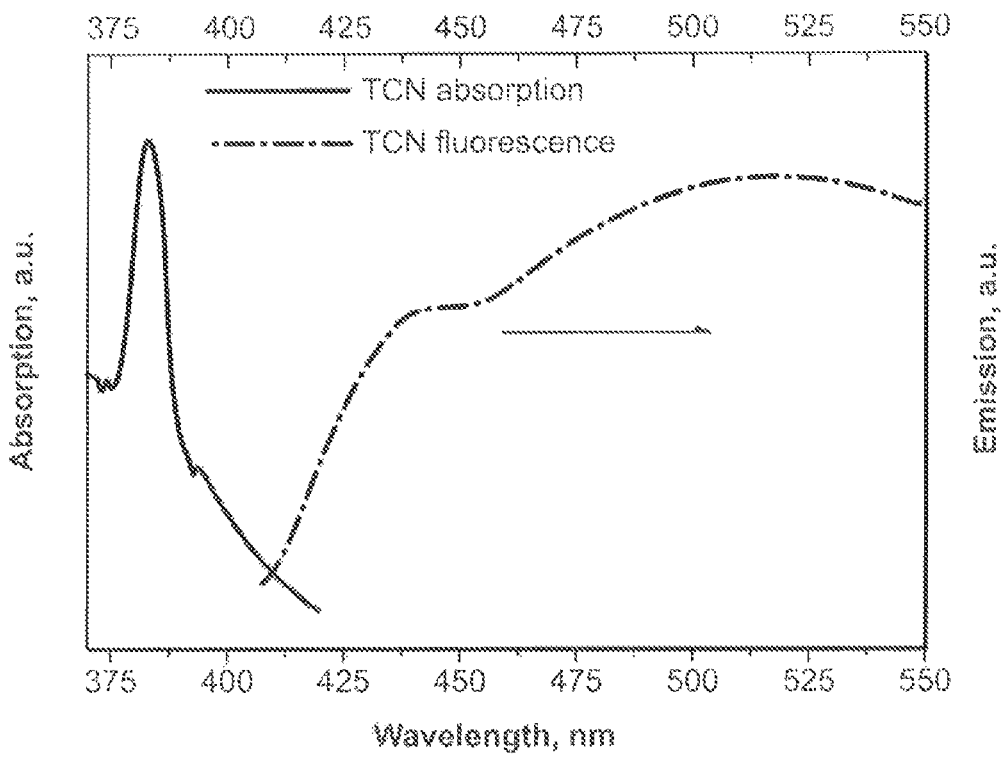
FIGS. 2A and 2B illustrate the excitation and absorption spectra of TCN and EY, respectively.
Figure 2B:
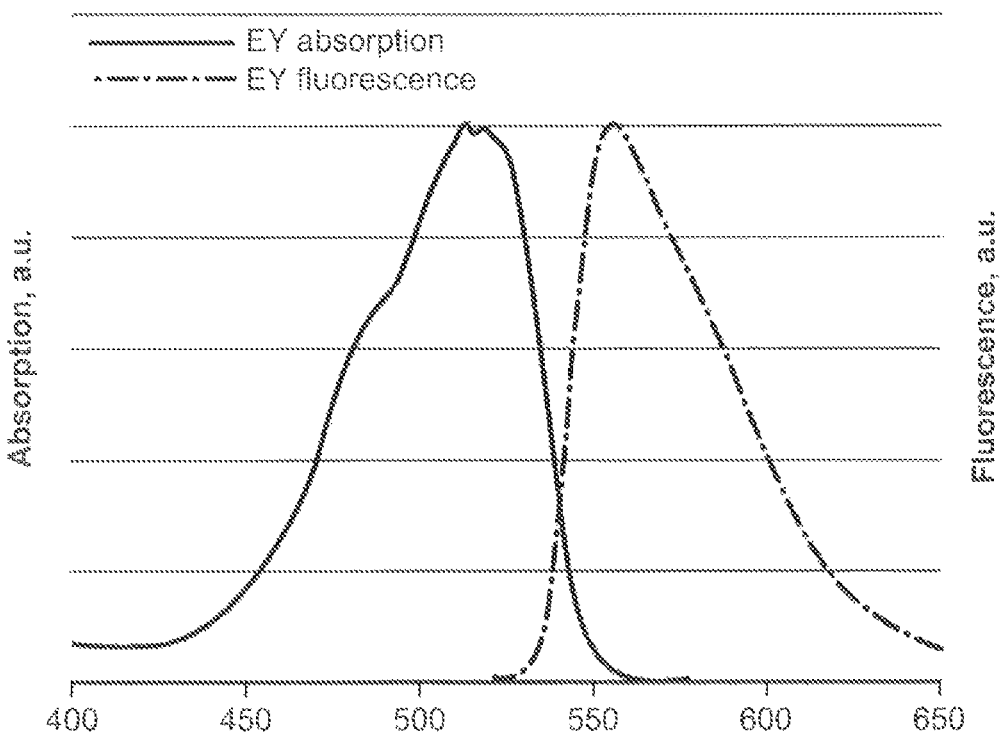

FIGS. 2A and 2B show the absorption and fluorescence spectra of TCN and EY, respectively. In general, light sources can be used that emit at a wavelength band in the ultraviolet visible and/or infrared that will induce fluorescence.

Figure 3:
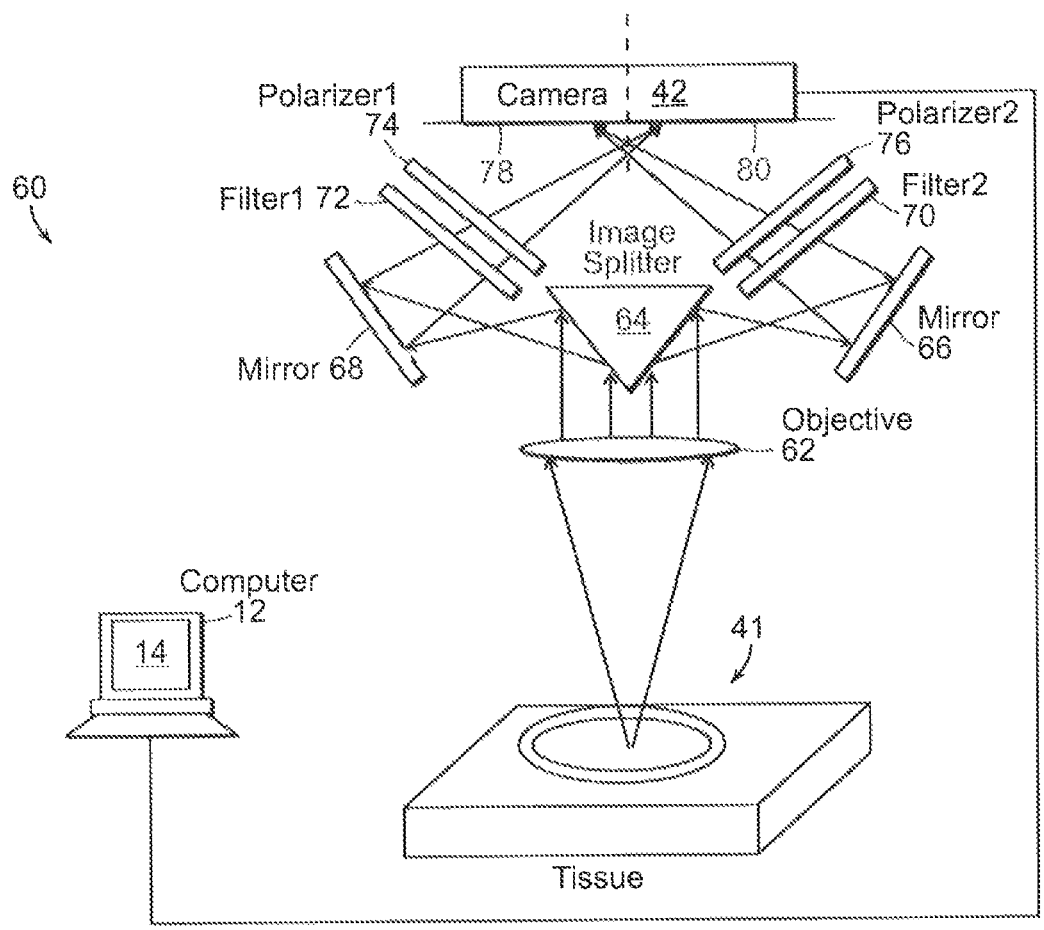
FIG. 3 illustrates a four-way image splitter used with an electronic imaging detector to obtain wide field high resolution images.

Shown in FIG. 3 is a detailed view of imaging system that splits the field of view to observe a plurality of polarization components with a single imaging detector. Two (or four) images can be obtained to view the different spectral regions and the different polarization components corresponding to the data collected by the photomultiplier tubes 20, 22, 24, 26.

The objective lens 62 collects the image from the tissue surface 41 which is split by image splitter 64. the two (or four) image components are reflected by mirrors 66, 68 through filters 70, 72, respectively. Polarizers 74, 76 can also be used to separate the polarization components, if desired. A plurality of images are detected on separate regions 78, 80 of the detector.

To determine the axial resolution a mirror can be used and the lateral resolution can be determined using a Ronchi Ruler of 600 line pair per mm. Fluorescent phantoms can be used as well as ex vivo skin and brain tissue stained in TCN and EY.

Since fluorescence anisotropy images are acquired and quantified, the modified system needs to be calibrated. The new G factor, to account for different transmission and detection efficiencies by the instrument for horizontal and vertical polarization, has to be determined. To do this, TCN and EY will be separately mixed with two solvents, one with high viscosity and one with low viscosity.

Computer 12 is used to record image data from the PMTS and the CCD. A display 14 can be located in the surgical operating room as well as at a remote location. Dedicated software in LabView and C can be used for automated image acquisition, processing and presentation.

Currently, the standard of care for diagnosing and delineating almost any type of pathology requires processing H&E (Hematoxylin & Eosin) histopathology, which involves excising and freezing suspicious tissue, cutting it in thin, 5 µm slices, placing these thin pieces on the slides, multistage staining, and cover slipping these slides. Then the slides are inspected and analyzed under the microscope by a certified pathologist. Hematoxylin is a basic dye and shows up in the acidic part of the cell like the nucleus, where nucleic acids (DNA and RNA) are concentrated. Therefore, hematoxylin is used to demonstrate nuclear and cytoplasmic structures. Eosin is used as a counterstain to hematoxylin. Eosin is an acidic dye and shows up in the basic parts of the cell, i.e. the cytoplasm. Eosin also stains collagen, muscle tissue and red blood cells. Hematoxylin is toxic and cannot be applied in vivo, whereas eosin is approved for human use.

The system can collect images at a rate of at least 10 frames per second and preferably at video rate of 30 frames per second or more. Using an objective lens of 60× a field of 250×250 microns can be imaged. An objective lens of 20× can yield an image of 800×800 microns, for example. The wide field CCD images can be obtained in less than 10 msec with a width of field of 2-3 cm. Wider fields up to 10-15 cm can also be obtained with suitable optics. The depth of the image slice is generally about 0.5 mm. However, slices can be selected in a range of 0.01 mm to 0.1 mm depending on the size of the field and scanning speed. In general, the depth of the image volume and the size of the image volume can be selected by the user based on the shape of the margin to be assessed. The images can be registered relative to each other to obtain composite color images of both stains.

Figure 4:
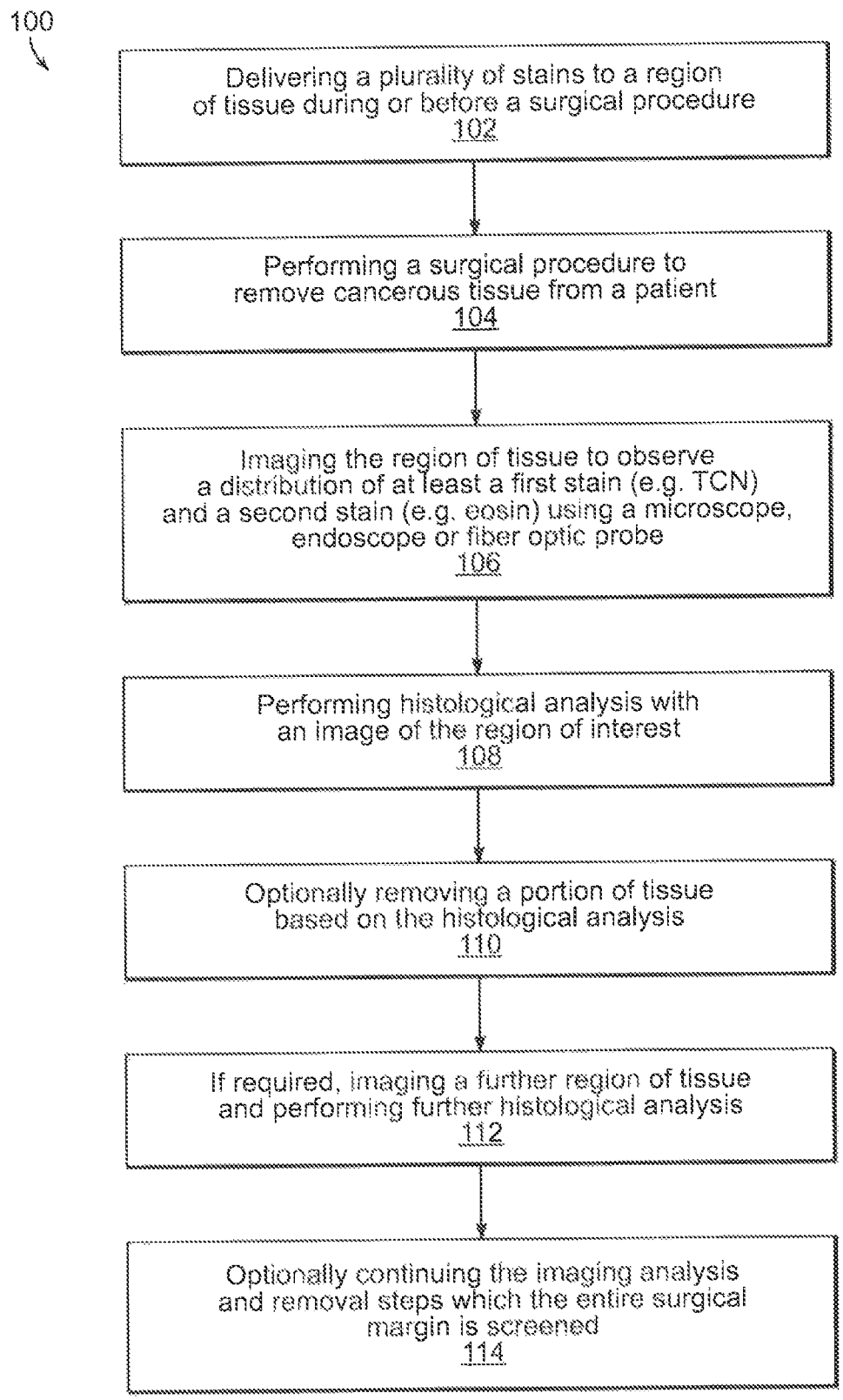
FIG. 4 is a process sequence illustrating a preferred method of interpretive histological examination of a patient.

The method 100 illustrated in FIG. 4 uses the similarities of the staining patterns of hematoxylin and tetracycline (TCN). Tetracycline is approved for human use. Therefore, it can be used in vivo. Eosin is an example of a stain that can be used as an in vivo counterstain to TCN. Thus, non-toxic stains are to be employed in connection with preferred embodiments of the invention.

The above mentioned fluorescent agents can be introduced 102 into the human body topically (application or), systemically, or through injection, depending on the body site, type of pathology, and medical procedure. After sufficient amount of dye is accumulated in the tissue of interest, during a surgical procedure 104 fluorescence and/or fluorescence polarization images can be registered using the system shown in FIG. 1. Upon completing image acquisition, fluorescence of the nuclei and cytoplasm stains will be color-coded and presented in the same image (either macro-, high-resolution, or both). Fluorescence polarization images will also be displayed in which the nucleus stain indicates locations of cancer lobules and cytoplasmic stain to indicate alterations of collagen, muscle tissue and cytoplasm. Histological analysis 108 of the images of the region of interest is used to assess the need for the removal of 110 of further tissue. The imaging, analysis and removal steps can be repeated 112 until the entire margin of the surgical site has been screened 114.

To enhance the contrast of optical images we used a phenothiazine dye, methylene blue, which is FDA-approved for human use. This dye has been successfully employed for gross-demarcation of neoplastic tumors in bladder, pancreas, and skin. MB has also been shown to closely mimic hematoxylin and eosin (H&E) staining pattern of histopathology in vivo and ex vivo. Measurements with systems configured in accordance with preferred embodiments of the invention used commercially available methylene blue (MB 1% injection, USP, American Regent Laboratories, Inc., Shirley, N.Y.) that was diluted to a concentration of 0.05 mg/ml with Dulbecco phosphate buffered saline solution (DPBS 1×, pH 7.4, Mediatech, Manassas, Va.).

The measurements were performed utilizing excess breast tissue that was obtained following surgical resection of breast tumors. The size of fresh tissue samples ranged from 20 mm to 150 mm and the thickness from 3 mm to 7 mm. Specimens were soaked in 0.05 mg/ml DPBS solution of MB for approximately 10 minutes and then rinsed in DPBS to remove excess dye. The stained tissues were imaged using the wide-field imaging system and the high resolution confocal microscope. After imaging, the tissue was fixed in formalin and processed for en-face H&E paraffin embedded histopathology.

Horizontal paraffin embedded histopathology sections were prepared from the imaged tissue samples. Five micron-thick sections were transferred to glass slides and stained with H&E. These H&E sections were digitized using Zeiss Axioscope microscope (Zeiss, Germany) equipped with a 5× objective lens, NA 0.13 (Zeiss, Germany) and an oil immersion 40× objective lens, NA 1.0 (Zeiss, Germany) for comparison to wide-field images and high-resolution mosaics, respectively. The optical images were correlated with histopathology obtained from approximately the same depth of the specimen.

Figure 5A:
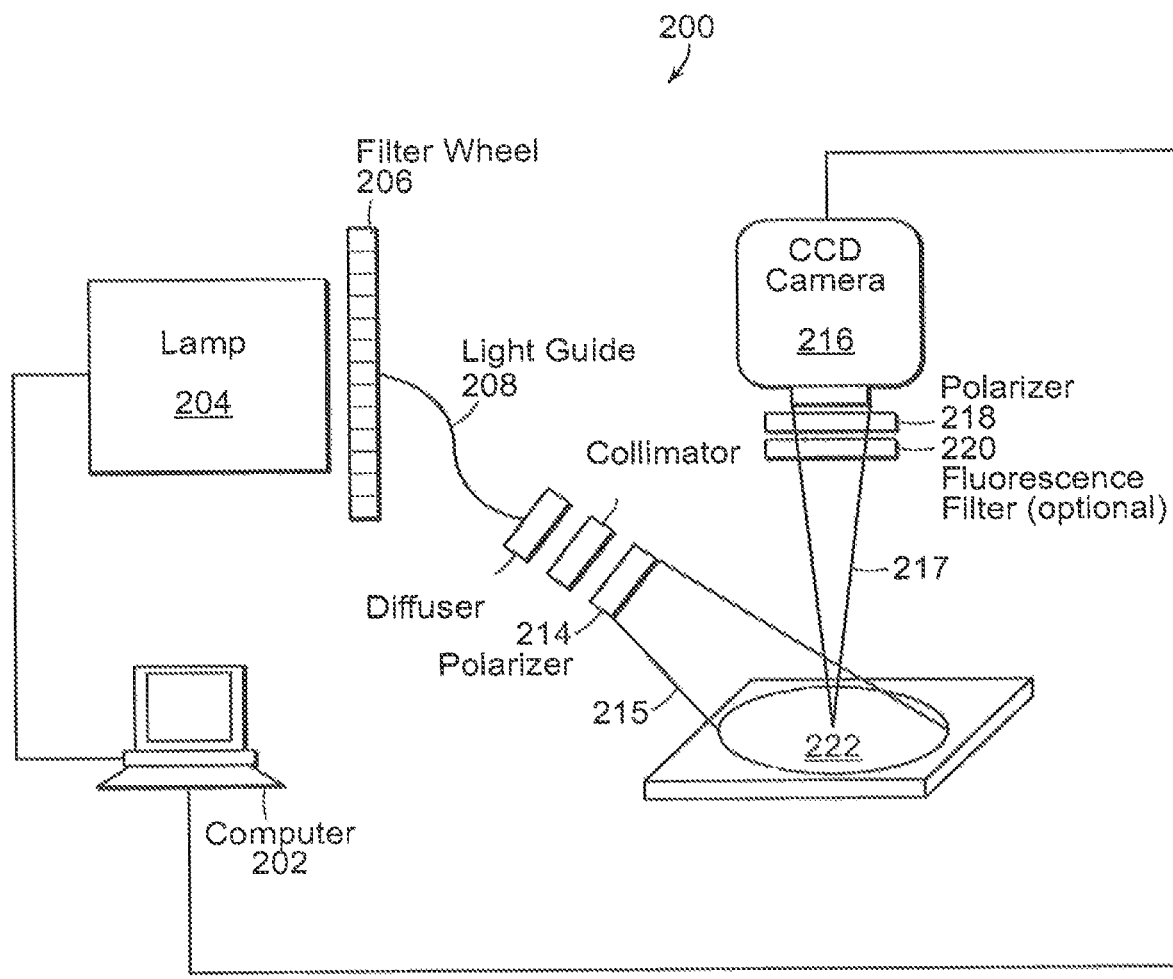
FIGS. 5A and 5B schematically illustrate a wide-field imaging system and the confocal imaging system, respectively.

A polarization enhanced wide-field imaging device 200 was used to assess tumor margins on a macroscopic scale. A schematic of the system is presented in FIG. 5A. A broadband light source 204 such as a xenon arc lamp (Lambda LS, Sutter, Novanto, Calif.) combined with 9 narrow bandpass filters 206 that can be mounted on a filter wheel, with full width at half maximum of 10 nm, that covered wavelength range from 390 nm to 750 nm was used as an illuminator. A 0.5× Rodenstock lens coupled to a CCD 216 camera (CoolSnap Monochrome Photometrics, Roper Scientific, Tucson, Ariz.) was used for image acquisition. Linearly polarizing filters (Meadowlark Optics, Frederick, Colo.) were employed in pathways of the light incident on the sample and for filtering 220 light collected by the camera. A fiber optic light guide 208 can be used for light delivery. Reflectance co- and cross-polarized images were acquired at the selected wavelengths (λ390 nm, 440 nm, 500 nm, 577 nm, 600 nm, 620 nm, 640 nm, 680 nm, 750 nm). Polarizers f214 and 218 are positioned as needed in the light delivery 215 and light collection 217 paths for the acquisition of the polarization components. Fluorescence co-polarized and cross-polarized images were excited at 640 nm and registered between 660 nm and 750 nm using an additional bandpass filter (660AELP, Omega Optical, Brattleboro, Vt.) placed in the pathway of the light remitted from the tissue. Co- and cross-polarized images were registered with an analyzing polarizer oriented parallel (co) and perpendicular (cross) to the polarization of the incident light. In the described configuration, the system allowed for a field of view 222 of 2.2 cm×1.6 cm, and a lateral resolution of approximately 30 μm. Generally, a field of view of at least 2 cm² and preferably 4 cm² or more if desirable to provide a wide enough field of view for many applications of margin assessment. For accurate detection of the two orthogonally polarized components of reflectance and fluorescence, the system was calibrated within a calibration factor, G, determined to be 0.98.

Fluorescence polarization images were calculated using the formula:

$$I_{fpol} = \frac{If_{co} - G \times If_{cross}}{If_{co} + G \times If_{cross}}$$

where $I_{fpol}$ is a fluorescence polarization image, G is the calibration factor (G=0.98), $If_{co}$ and $If_{cross}$ are co- and cross polarized fluorescence emission images.

Reflectance polarization images were calculated using the formula:

$$I_{pli} = \frac{I_{co} - G \times I_{cross}}{I_{co} + G \times I_{cross}}$$

where $I_{pli}$ is a reflectance polarization image, G is the calibration factor (G=0.98), $I_{co}$ and $I_{cross}$ are experimental co- and cross polarized reflectance images. A computer or data processor 202 can be used for image processing and system control functions.

Averaged polarization values, reflectance and fluorescence, for cancerous and normal tissue regions were obtained. Cancerous and normal regions were grossly outlined by a pathologist in digitized histopathology slides. Due to the preparation of paraffin embedded histopathology, sections may be stretched or shrunk in comparison to wide-field images. To correct for this artifact, digitized histopathology slides were overlaid onto wide-field images. Then affine, projective, or polynomial transformations were applied so that similar structures in the wide-field images coincided with corresponding structures in histopathology. After correction, the regions corresponding to cancer and normal breast tissue in histopathology were outlined in the wide-field reflectance and fluorescence polarization images. Mean reflectance and fluorescence polarization values for cancer and normal areas were obtained for each specimen. These values were averaged over all specimens, to obtain the mean fluorescence polarization of cancer and normal tissue.

Figure 5B:
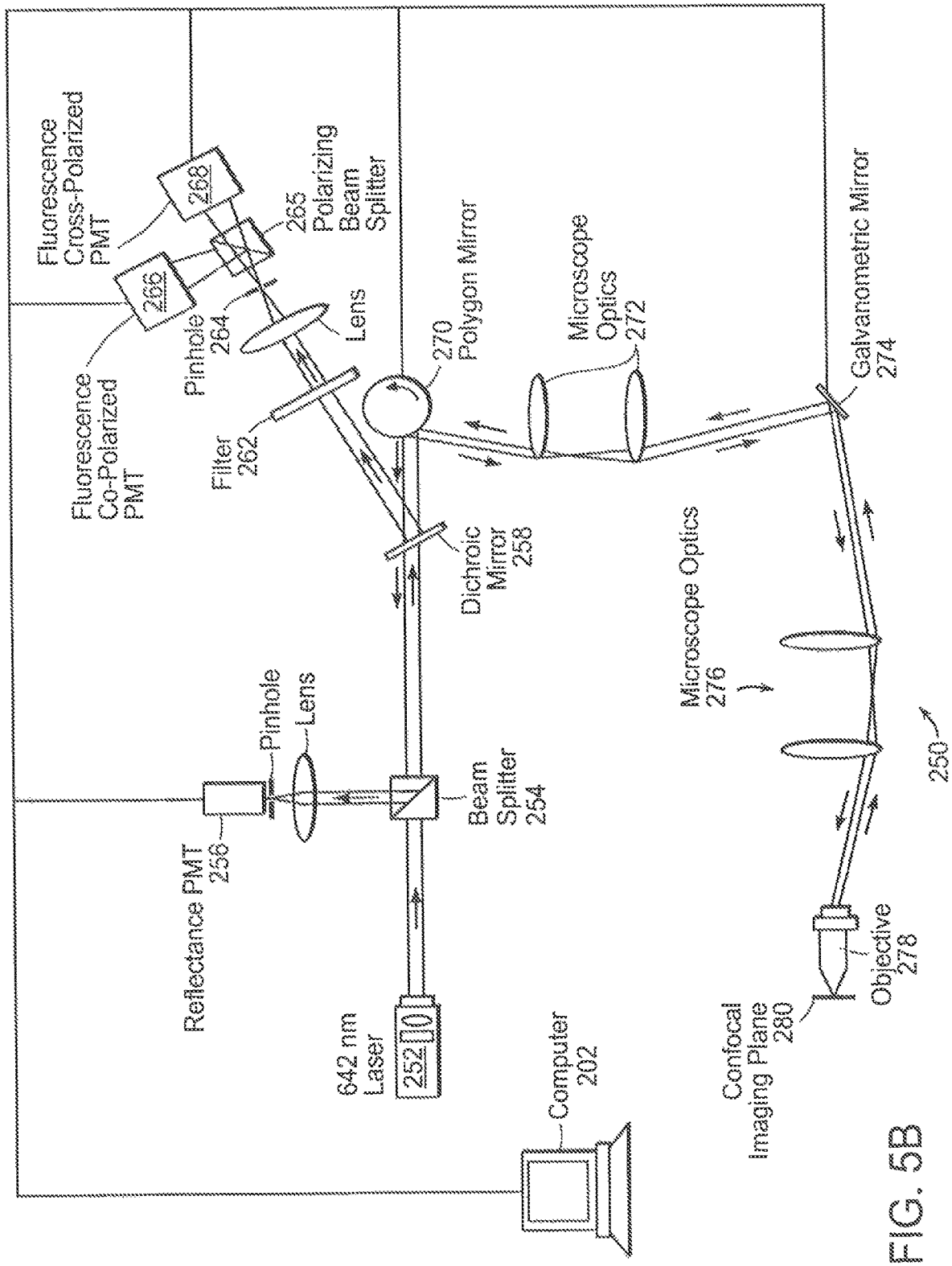

The schematic of the confocal microscope system 250 is shown in FIG. 5B. Linearly polarized collimated light emitted by a 642 nm diode laser light source 252 (MicroLaser Systems, Garden Grove, Calif.) was used for illumination. Three photomultiplier tubes 256, 266, 268 (PMT R9110 Hamamatsu, Bridgewater, N.J.) were used for the simultaneous multimodal signal detection, including reflectance, co- and cross-polarized fluorescence signals. This point scanning system utilized a scanning assembly 270 such as a moving polygon mirror (Lincoln Laser, Phoenix, Ariz.) for fast scanning along x-axis and a galvanometric mirror 274 (General Scanning INC., Billerica, Mass.) for slow scanning along y-axis. The signal remitted from the tissue was focused onto the 12° dichroic mirror 258 Iridian Spectral technologies, Ottawa, Ontario), which transmitted the elastically scattered and reflected fluorescence emission signal. An additional narrow bandpass filter 262 (690 nm±20 nm, Chroma Technology Corp, Bellows Falls, Vt.) was positioned in the path of the fluorescence channel to further reject excitation light. A lens focused the fluorescence signal onto the 200 µm pinhole 264. Polarizing beam splitter 265 (Karl Lambrecht Corporation, Chicago, Ill.) divided co- and cross-polarized fluorescence emission into their respective detectors or PMT's. The reflectance signal was deflected by a non-polarizing 95/5 beam splitter 254 (CVI Melles Griot, Albuquerque, N. Mex.) and focused onto the 200 µm pinhole of the reflectance channel PMT by a lens. An Olympus air-immersion 40×/0.6 NA and water immersion 40×/1.15 NA lenses 278 were used for imaging. The system provided a field of view of 350 µm×350 µm, axial resolution of 3-6 and a lateral resolution better than 0.9 µm in the range from 600 nm to 830 nm. Microscopic optics 272, 276 were used to couple the scanning beam into the objective lens and onto the confocal imaging plane 280 within the tissue.

The confocal system exhibited 250 different efficiencies for the detection of different polarization states of the light. To enable accurate quantitation of the fluorescence polarization, the imager was calibrated. The calibration factor, G, for the confocal system was determined to be 1.2. Reflectance and fluorescence images were acquired simultaneously at a rate or 9 frames per second.

To evaluate and compare MB fluorescence polarization exhibited by cancer and normal cells we manually outlined well defined cancer and normal cells in the confocal fluorescence co- and cross-polarized images, averaged the pixel values across the cell area, and applied fluorescence polarization equation (1). Then fluorescence polarization values obtained for different types of cells were grouped by the type (cancer and normal) and averaged. Averaged fluorescence polarization values of cancerous cells were compared with those of normal cells.

To quantify the significance of differences between the fluorescence polarization values of cancerous and normal breast tissue, we statistically evaluated the data using a 1 tailed student's t-test for 2 independent populations. Significance tests were performed on wide-field and confocal fluorescence polarization data. For wide-field imaging mode, we tested the alternative hypothesis that the mean fluorescence polarization value averaged over cancer regions of the specimens was greater than that averaged over the normal regions of the specimens. The analysis was performed separately for ductal and lobular carcinomas, as well as for all the samples investigated. For confocal imaging mode, we analyzed the statistical significance of the fluorescence polarization differences between cancer and normal cells for one ductal carcinoma specimen.

Figure 6G:
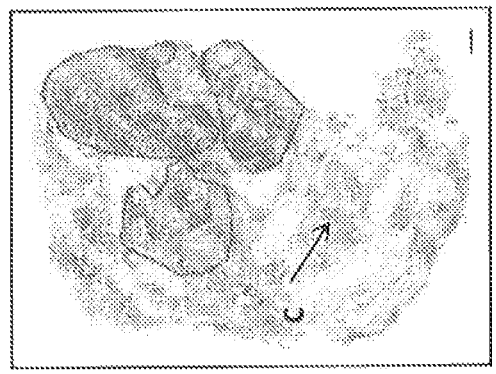
FIGS. 6A-6G are wide-field optical and histopathology images of a sample with intracystic papillary carcinoma; t: tumor; c: connective tissue; scale bar: 1 mm.
Figure 6C:
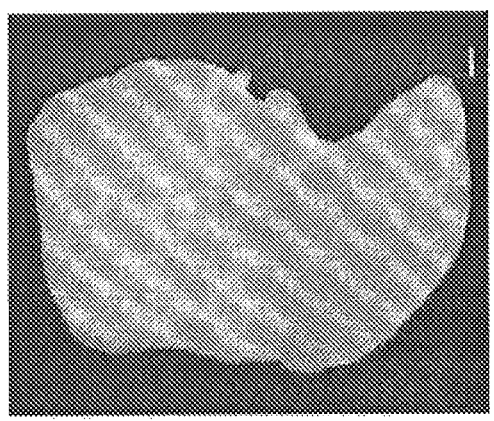
Figure 6F:
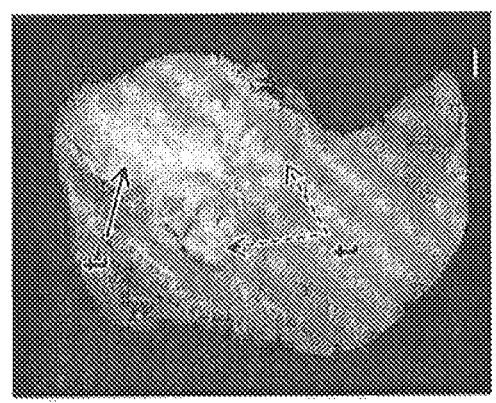
Figure 6B:
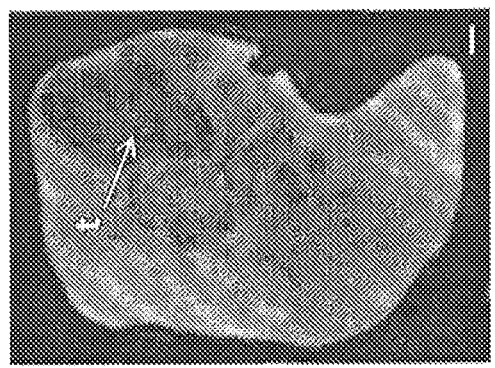
Figure 6E:
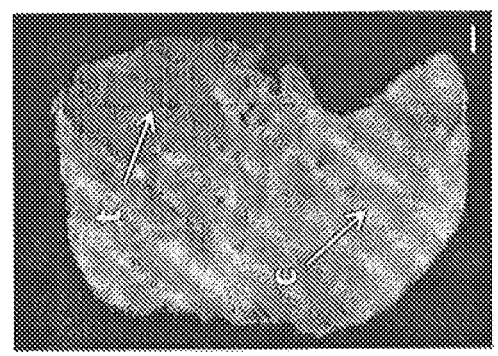
Figure 6A:
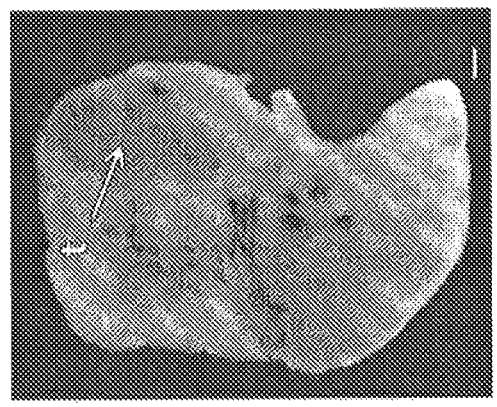
Figure 6D:
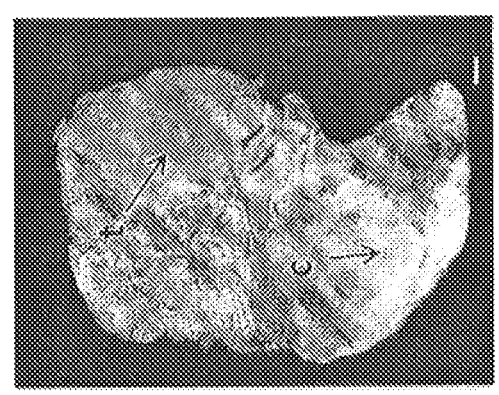

In total, 17 samples were imaged, of which there were 12 ductal carcinomas (11 invasive and 1 intracystic papillary (in-situ) carcinoma) and 5 lobular carcinomas (all invasive). Wide-field optical images of a representative sample with ductal carcinoma are presented in FIGS. 6A-6G. This is intracystic papillary carcinoma, which remains confined within the breast ducts. Reflectance and reflectance polarization images acquired at 440 nm are shown in FIGS. 6A and D, respectively. As 440 nm lies outside the absorption band of MB, reflectance images registered at this wavelength look similar to those of unstained tissue. Comparison of reflectance (FIG. 6A) and reflectance polarization (FIG. 6D) images demonstrates that optical sectioning afforded by polarization imaging significantly improves the resolution and level of detail discernable in the image. All backscattered photons may contribute to the conventional reflectance image, whereas only single backscattered photons form the reflectance polarization image. The depth of polarization imaging is defined by the inverse of the reduced scattering coefficient of breast tissue. Using optical properties of bloodless breast tissue reported in the literature, we have estimated the imaging depth of polarization macro-imaging to be approximately between 320 µm-620 µm in the visible spectral range.

The 640 nm reflectance images (FIG. 6B, 6E) show increased uptake of the dye within the tumor, which results in stronger attenuation of remitted light within the MB absorption band. Similarly to the reflectance images acquired at 440 nm (FIGS. 6A, D), the 640 nm reflectance polarization image (FIG. 6E) provides higher resolution, relative to the conventional reflectance image (FIG. 6B—640 nm). However, comparison to histopathology presented in FIG. 6G demonstrates that smaller ducts with tumor (outlined), marked with dashed arrows in histopathology, were not revealed in reflectance images as they were concealed by the highly scattering connective tissue.

Wide-field fluorescence emission and fluorescence polarization images of the intracystic papillary carcinoma are presented in FIGS. 6(C, F). Fluorescence emission image (FIG. 6C) shows that although dye uptake in the tumor is higher as compared to normal tissue, the concentration of MB in normal areas is considerable. As a result, the wide-field fluorescence emission image (FIG. 6C) does not allow for reliable delineation of cancer. In contrast, fluorescence polarization image (FIG. 6F) clearly demarcates a large tumor mass, as well as smaller tumor nests (dashed arrows). These smaller tumor nests are clearly defined only in the fluorescence polarization image (FIG. 6F).

Comparison of the images presented in FIGS. 6A-6F demonstrates that the level of detail provided by wide-field polarization reflectance and fluorescence imaging is critical for adequate correlation to histopathology and accurate tumor demarcation.

Figure 7A:
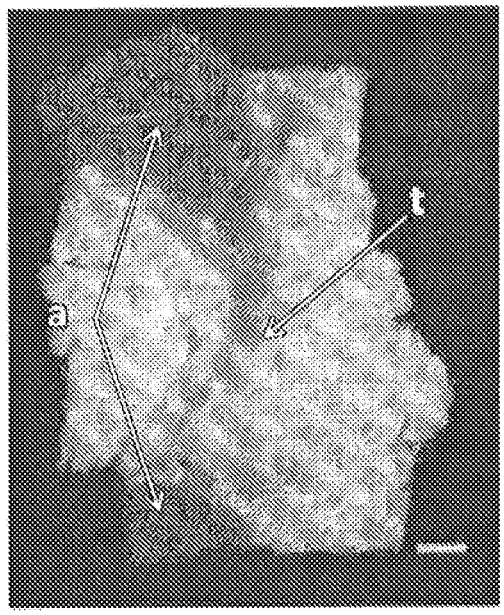
FIGS. 7A-7D are wide-field optical and histopathology images of a sample with grade III invasive ductal carcinoma; t: tumor; a: adipose tissue; scale bar: 1 mm.
Figure 7B:
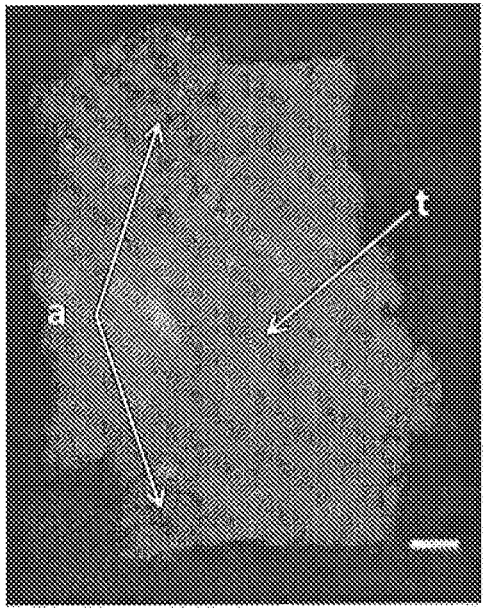
Figure 7C:
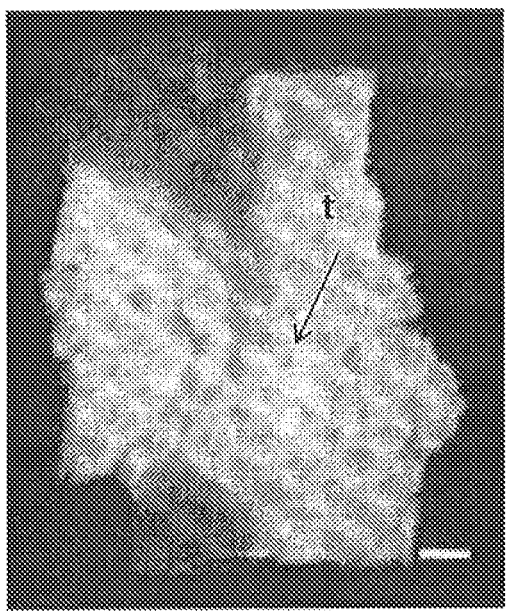
Figure 7D:
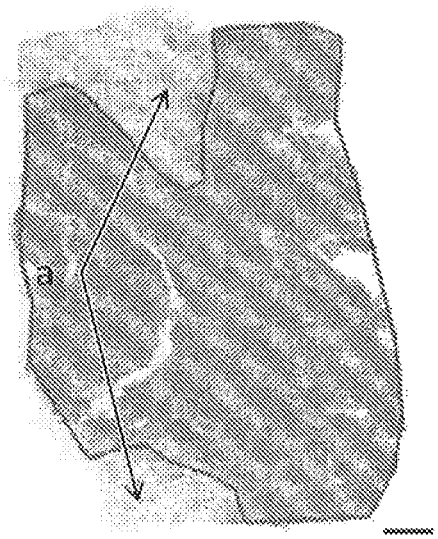

Invasive ductal carcinoma is the most frequently observed type of breast cancer. This cancer is characterized by abnormal proliferation of breast ducts and infiltration of the malignant glands into the surrounding residual breast normal tissue. Wide-field images of a representative sample with grade III invasive ductal carcinoma are presented in FIG. 7A-7D. The 440 nm reflectance polarization image (FIG. 7A) indicates higher scattering of the tumor relative to adipose tissue. Reflectance polarization image acquired at 640 nm (FIG. 7B) demonstrates preferential accumulation of MB in the tumor as compared to adipose tissue. Fluorescence polarization image, presented in FIG. 7C, reveals a large tumor mass bordered by pockets of adipose tissue, which appear dark due to the low uptake of MB. Comparison with histopathology, presented in FIG. 7D, shows that all three images, i.e., 440 nm reflectance polarization, 640 nm reflectance polarization and fluorescence polarization, correctly delineate tumor margins. The size, shape and location of cancer nodules in reflectance and fluorescence polarization images correlate well with those identified in the H&E histopathology. However, due to high absorption of MB and low scattering of adipose tissue, 640 nm reflectance polarization image exhibits lower contrast, as compared to 440 nm reflectance polarization and fluorescence polarization images. Due to higher scattering, which warrants better optical sectioning, 440 nm reflectance polarization facilitates higher resolution as compared to fluorescence polarization image. At the same time, due to very low MB uptake of adipose tissue, fluorescence polarization image (FIG. 7C)

provides higher contrast as compared to the 440 nm reflectance polarization image (FIG. 7A).

Invasive lobular carcinoma is the second most common form of breast cancer. It typically infiltrates as tumor cells arranged in single files surrounded by a fibrous stroma and may not form a discrete mass. This type of breast cancer is therefore more difficult to delineate due to the diffuse infiltrative pattern of growth. Wide-field images of a representative specimen with invasive lobular carcinoma are presented in FIG. 8A-8D. Wide-field reflectance polarization imaging at 440 nm (FIG. 8A) revealed fibrous, adipose, and connective tissue structure. Comparison to the corresponding H&E section, shown in FIG. 8D, demonstrates that 440 nm reflectance polarization image does not allow for the detection of the tumor. The 640 nm reflectance polarization image (FIG. 8B) highlighted areas of increased dye uptake. However, the location of these areas did not correlate well with location of cancer areas in histopathology (FIG. 8D). In contrast, the fluorescence polarization image (FIG. 8C) clearly outlines the large tumor bordering connective and adipose tissue. The location, size and shape of cancer correlate well with those in histopathology. Out of the 3 optical images (FIGS. 8A-C), fluorescence polarization provides the best correlation with histopathology and offers the highest contrast of the tumor with respect to normal tissues.

Confocal fluorescence emission mosaics of the ductal and lobular carcinomas examined using wide-field imaging (FIGS. 7A-7D and 8A-8D) are presented in FIGS. 9A-9G and FIGS. 10A-10G. Mosaics of the entire specimens are shown in FIGS. 9A and 10A. Their appearance is similar to the wide-field fluorescence images shown in FIGS. 8C and 7C, respectively. Comparison of confocal mosaics with histopathology shows good correlation. Similarly to wide-field images, confocal mosaics grossly outline the tumor margins. However, as resolution provided by confocal microscopy is superior to that of wide-field technique, confocal images readily lend themselves to straight forward comparison with histopathology at the cellular level.

Fluorescence emission confocal mosaics of the smaller fields or subregions within the lobular specimen outlined with squares in FIG. 9A are presented in FIGS. 9B, C, and D along with corresponding histopathology shown in FIGS. 9E, F, G. The tumor/adipose boundary can be accurately outlined as shown in FIG. 9B. Fat pockets separated by connective tissue, septa, as well as single cancer cells exhibit high contrast and can be clearly resolved in both fluorescence emission images (FIG. 9B) and histology (FIG. 9E). Diffuse tumor growth, indicative of lobular carcinoma, can be seen in the FIG. 9C, where small tumor cells are scattered around a vessel. In FIG. 9D, confocal imaging reveals an aggregate of lymphocytes, crowded around the blood vessel. Comparison of the confocal images shown in FIGS. 9C and D demonstrates good correlation with histopathology (FIGS. 9F, G). Fluorescence emission confocal mosaics of the small fields within the ductal specimen, outlined with squares in FIG. 10A, are presented and compared to corresponding histopathology in FIGS. 10B-G. The margin between tumor cluster and adipose tissue can be accurately delineated in FIG. 10B. Unlike cancer margins of lobular carcinoma shown in FIG. 9A, the boundaries of ductal carcinoma do not present diffuse cancer infiltration and can be clearly outlined without analyzing cellular detail. Images presented in FIGS. 10C and D show densely packed tumor cells, which are separated by strands of connective tissue. Close correlation between optical and histology images can be readily appreciated.

Figure 11:
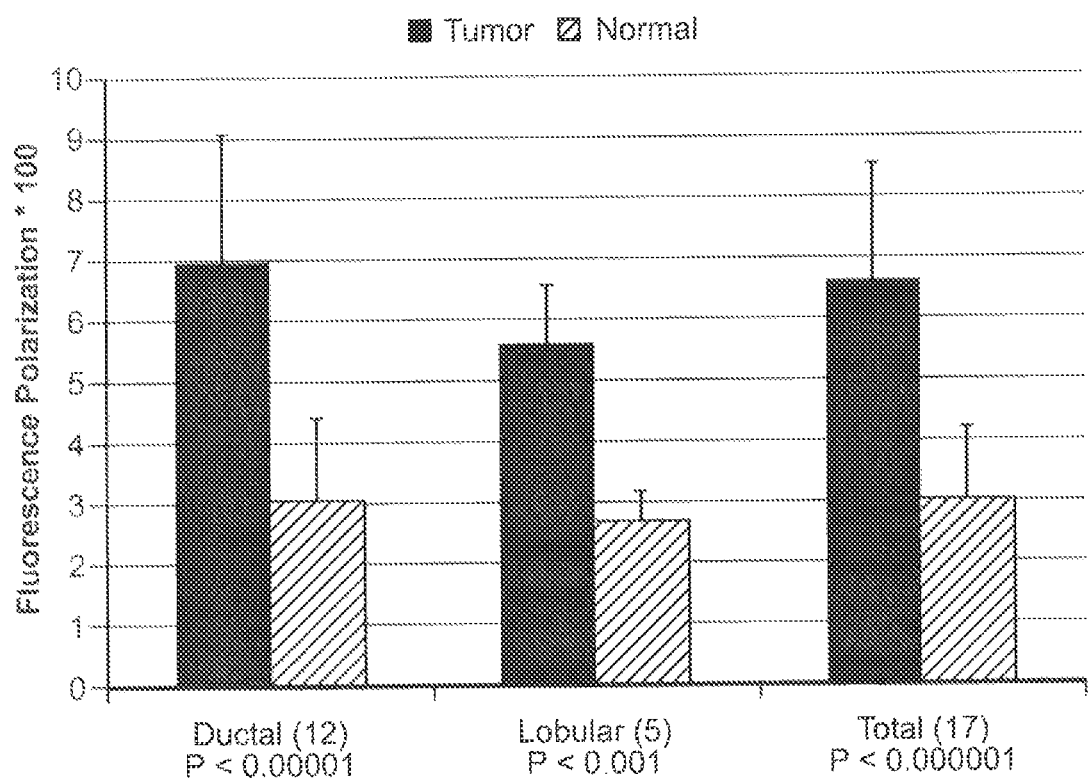
FIG. 11 illustrates fluorescence polarization values (×100) for cancerous (dark gray) and normal (light gray) breast tissue averaged over all samples; bars show standard deviations and P-values are given for student's t-test of two independent populations.

Fluorescence polarization values for tumor and normal areas averaged over all samples are summarized in FIG. 11. For all the specimens investigated, wide-field fluorescence polarization exhibited by cancerous higher as compared to normal tissue. More importantly, the location, shape and size of the tumor area outlined in fluorescence polarization images correlated well with those in respective histopathology. Ductal and lobular carcinomas exhibited comparable values of fluorescence polarization. Statistical analysis confirmed that the differences in fluorescence polarization averaged over tumor and normal tissue regions were significant for both ductal ($p_{ductal}$<0.00001) and lobular ($p_{lobulat}$<0.001). A higher fluorescence polarization signal from cancer is the result of lower fluorescence depolarization of the incident signal in the tumor as compared to normal breast. Fluorescence depolarization is determined by the rotational diffusion of the fluorophore, MB, during its fluorescence life-time. Therefore, it depends on the viscosity of the environment and/or the binding state of the fluorophore. Another factor that may affect fluorescence polarization is scattering within the sample. Increased scattering yields decreased fluorescence polarization, as it randomizes polarization state of the detected signal. Both reflectance polarization images of the ductal (FIG. 7A) and lobular (FIG. 8A) carcinomas acquired at 440 nm showed that tumor affected areas were brighter than normal regions of the specimen, indicating higher scattering within the tumor. In particular, reflectance polarization values averaged over cancerous tissue are 0.14±0.03 and 0.16±0.06, whereas normalized reflectance polarization values averaged over normal structures are 0.08±0.02 and 0.12±0.04, for the ductal (FIG. 7A) and lobular (FIG. 8A) carcinomas, respectively. Analysis of the 440 nm reflectance polarization images shows that relative reflectance polarization of cancer is higher for ductal carcinoma. In particular, the averaged ratio of reflectance polarization of cancer to normal tissue for ductal carcinomas is equal to 1.8, whereas for lobular carcinoma it is equal to 1.3. Nonetheless, in both cases scattering from tumor dominates that from normal tissue. Higher scattering within the tumor should have led to lower fluorescence polarization of the signal from the tumor. In contrast our results demonstrate higher relative fluorescence polarization registered from cancer (FIGS. 6F, 8C, 11), even though scattering within cancer is higher than within normal tissue. This indicates that intrinsic fluorescence polarization of tumor is higher as compared to normal residual fibroadipose breast tissue. Our results reveal that binding of the fluorophore and/or viscosity within the tumor cause higher fluorescence polarization exhibited by cancer.

Figure 12A:
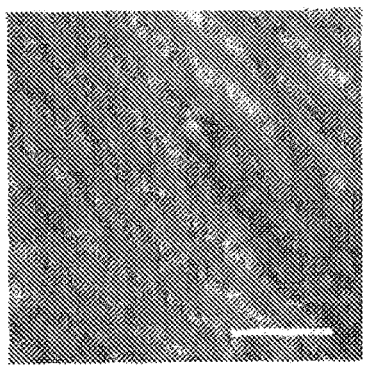
FIGS. 12A-12I are images of invasive ductal carcinoma; scale bar: 0.1 mm. Fluorescence emission of tumor (A), fibroblasts (B), and adipose tissue (C). Corresponding fluorescence polarization of tumor (D), fibroblasts (E), and adipose tissue (F). Histopathology of tumor (G), fibroblasts (H), and adipose tissue sections (I).
Figure 12B:
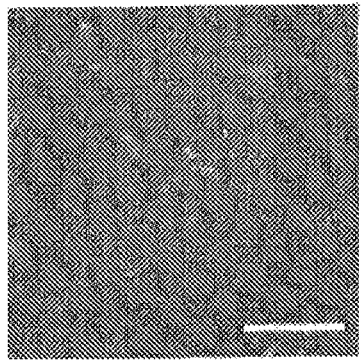
Figure 12C:
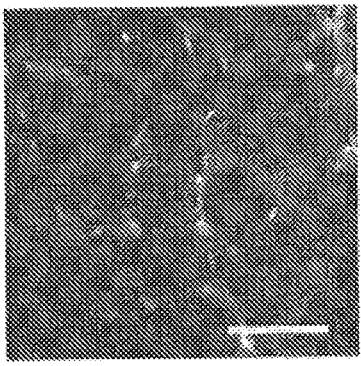
Figure 12D:
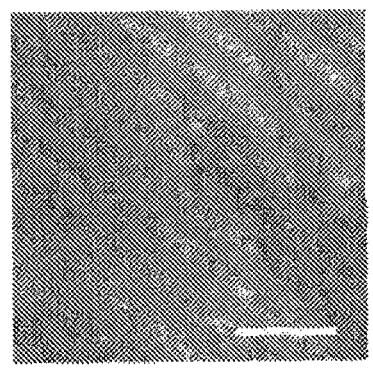
Figure 12E:
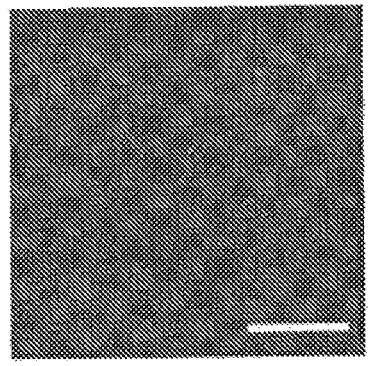
Figure 12F:
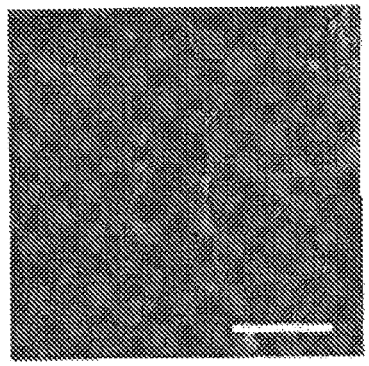
Figure 12G:
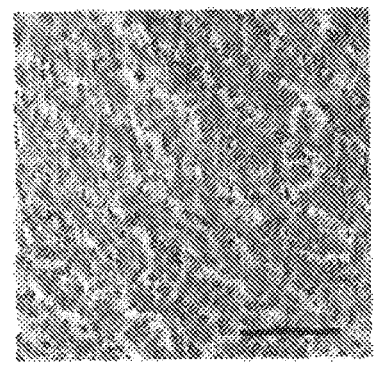
Figure 12H:
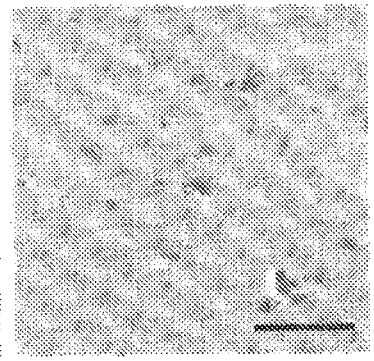
Figure 12I:
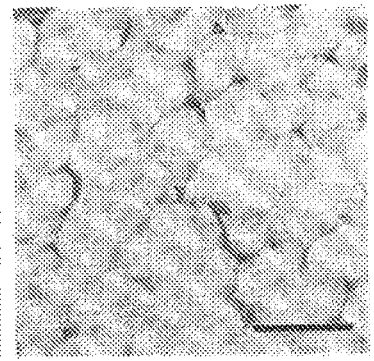
Figure 13:
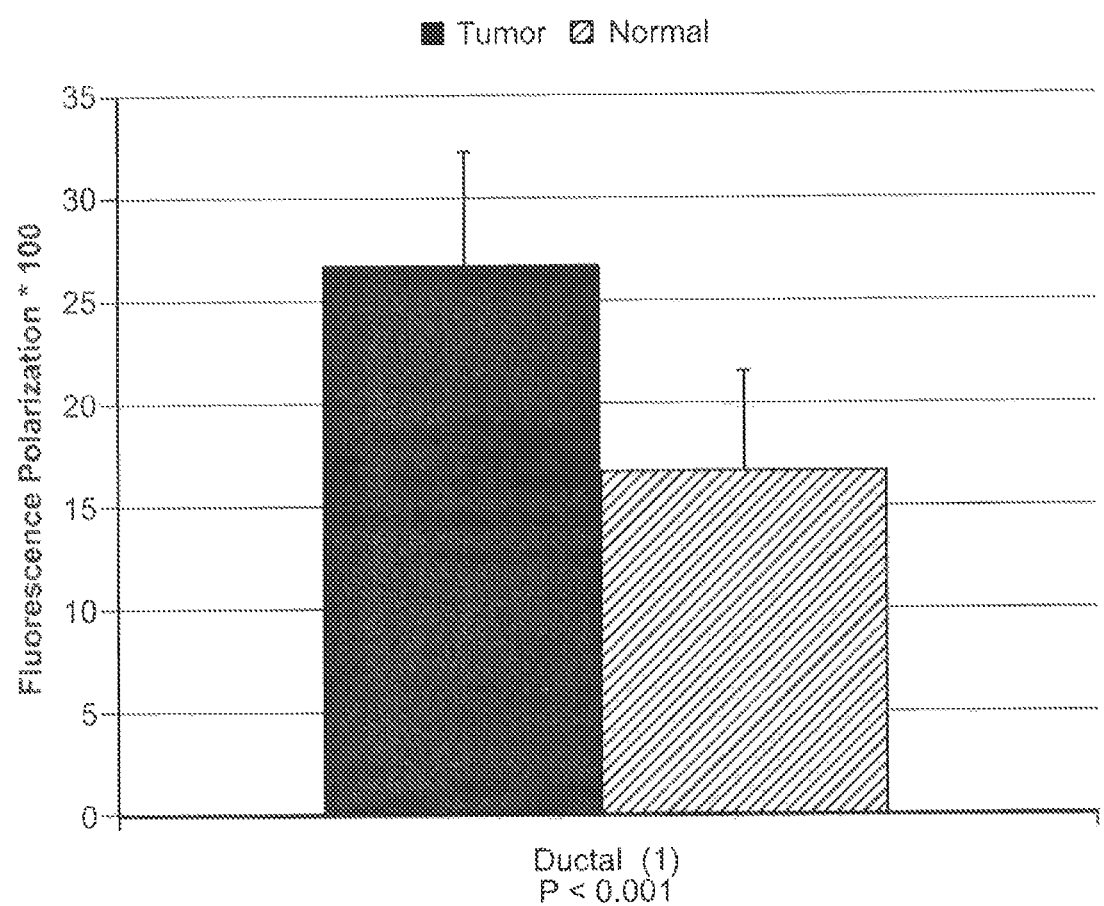
FIG. 13 includes fluorescence polarization values (×100) averaged over cancer (dark gray) and normal cells (light gray) of a ductal carcinoma specimen presented in FIGS. 12A-12I. Bars show standard deviations and the P value is given for student's t-test of two independent populations.

To evaluate fluorescence polarization on the cellular level, confocal fluorescence polarization images of a sample with invasive ductal carcinoma were processed, analyzed, and compared to respective histopathology. Representative fluorescence emission and fluorescence polarization confocal mosaics of cancer and surrounding residual normal breast tissue are presented in FIGS. 12A-F. Corresponding H&E histopathology is presented in FIGS. 12G-I. Comparison of fluorescence emission (FIGS. 12A-C) and fluorescence polarization images demonstrates that contrast of tumor cells remains high, whereas that of normal cells decreases in fluorescence polarization. Thus, fluorescence polarization imaging can assist in identifying cancer cells and distinguish tumor cells from normal. For cellular fluorescence polarization quantitation the representative areas were manually selected by comparing them with the H&E images. Only well-defined cancer and normal cells were analyzed. The analysis has shown that fluorescence polarization of tumor cells was 0.27±0.05. Fluorescence polarization of normal cells was found to be 0.16±0.05. Statistical analysis has shown that these differences are significant ($p \leq 0.001$). The results are summarized in FIG. 13. Comparison of FIG. 13 and FIG. 11, which summarizes respective results obtained from wide-field images, reveals that fluorescence polarization calculated from confocal images is higher for both cancer and normal tissue. In confocal imaging, multiple scattering does not contribute to randomization of fluorescence polarization. Therefore, the values of fluorescence polarization registered from single cancer and normal cells are higher as compared to those obtained using wide-field imaging. Thus, exogenous fluorescence polarization can be used to detect abnormal conditions in single cells such as cancer. Contrast agents, such as methylene blue or similar fluorescent stains, can be used to quantify exogenous fluorescence polarization of individual cancer cells. These methods can be used for cancer margin assessment as described herein.

These measurements provide dye-enhanced multimodal wide-field macroscopic and high-resolution confocal imaging for intraoperative detection and demarcation of breast cancers. The system acquire and analyze reflectance, fluorescence, and polarization images of a contrast MB stained ductal and lobular carcinoma tissue. The results indicate that topically applied aqueous solution of MB preferentially accumulates in cancer tissue and significantly enhances contrast of the optical images. Predictably, both reflectance and fluorescence wide-field polarization imaging allowed for better delineation of the superficial breast tissue structures, as compared to conventional reflectance and fluorescence emission, because polarization imaging enables optical sectioning of thick tissue. Reflectance and reflectance polarization images emphasized the structure of connective, fibrous and adipose tissues. However, in spite of considerable retention of MB in tumors, reflectance images did not delineate cancer margins reliably, most probably due to high scattering exhibited by breast tumors. In contrast, wide-field fluorescence polarization and high-resolution fluorescence emission imaging accurately revealed the location, shape, size and morphology of tumor in all 17 measured tissue regions. Fluorescence polarization of cancer, quantified from wide-field images, was reproducibly higher as compared to normal breast tissues. Similarly, as estimated from confocal images of a ductal carcinoma specimen, MB fluorescence polarization registered from cancer cells was significantly higher as compared to that of normal cells. Note that MB molecules bind to mitochondria, which are plentiful in cancer cells. This indicates why there is higher fluorescence polarization signal of MB in breast tumor cells.

The present invention provides for the use of complimentary reflectance, fluorescence and polarization wide-field and high-resolution imaging modalities for intraoperative breast cancer demarcation. Wide-field fluorescence polarization imaging enables rapid and accurate macroscopic delineation of breast cancer margins, but cannot provide resolution comparable to that of histopathology. Confocal fluorescence emission imaging enables microscopic analysis of the tissue morphology on the cellular level, but is limited by a less than millimeter field of view even for low 20× magnification. Acquiring multiple confocal images followed by assembling a mosaic of the entire specimen or surgical field requires considerable time. In addition, confocal mosaic represents a sizable amount of data, approximately 1.5 GB for an 8 mm×11 mm lobular carcinoma sample imaged at 40× (FIG. 9A). Besides, most of this data is not required for the delineation of cancer margins. Therefore, a combination of rapid digital imaging with confocal microscopy can enable fast, accurate and reliable intraoperative cancer demarcation, so that wide-field fluorescence polarization imaging grossly delineates tumor margins and guide high-resolution confocal inspection of cellular detail in suspicious areas.

Optical imaging has the advantage of preserving tissue, whereas in conventional histopathology, valuable tissue may be lost compromising final diagnosis on permanent sections. Furthermore intra-operative frozen section evaluation of breast cancer for assessing margins may not be practical as examining the entire surface is time consuming and not an efficient and reliable method. Additionally, optical imaging can be done in the surgical bed quickly and at a low cost thereby lowering the possibility of re-excision due to positive margins. Fluorescence polarization can be used for automated detection of breast cancer where a computer aided diagnosis employing reproducible range of fluorescence polarization values that are used for the different breast cancer types.

Thus, preferred embodiments of the invention provide an in vivo system capable of enabling complete and accurate image guided resections of cancer. Wide-field and high-resolution fluorescence and fluorescence polarization imaging are used in combination for intraoperative rapid and accurate breast cancer delineation.

As illustrated in FIG. 14A-14I, reflectance and fluorescence images can be combined to form fused pseudo-color images of tissue. In this embodiment, TCN is used as a cytoplasmic stain with illumination wavelengths in the range of 370-410 nm and MB is used as the nuclear stain with wavelengths in a range of 620-670 nm.

FIGS. 14A-14F also compare the fused pseudo color images to histological images of the same sample. Both reflectance and fluorescence images are obtained using the systems described herein. Image normalization can be performed, such as by contrast limited adaptive histogram equalization (CLAHE).

Figure 14A:
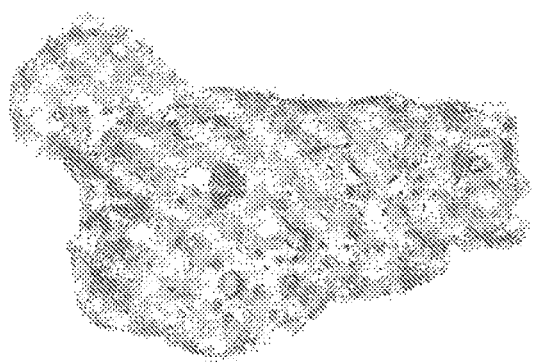
FIGS. 14A-14F show combined reflectance and fluorescence pseudo color images for skin cancer, breast cancer and brain cancer contrasted with standard histology images, respectively.
Figure 14B:
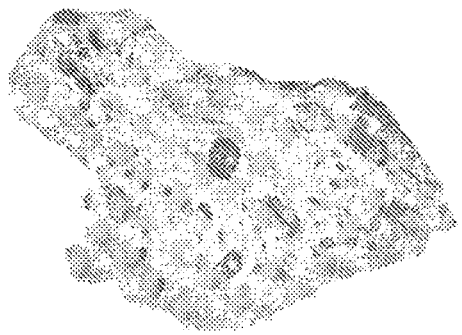
Figure 14C:
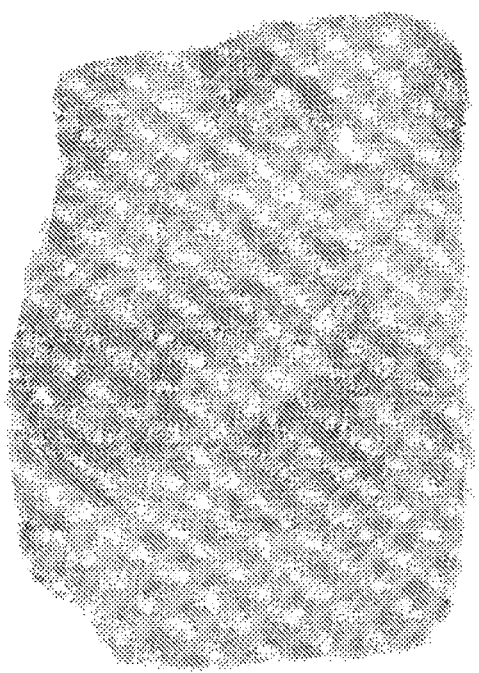
Figure 14D:
Figure 14F:
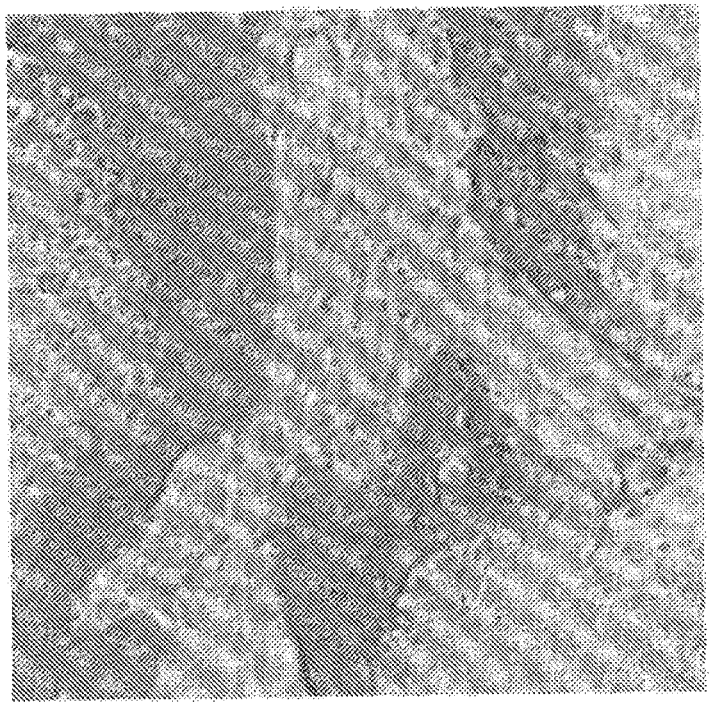
Figure 14E:

The two images can be combined or fused, which in the case of skin cancer tissue of FIGS. 14A and 14B, show pseudo color and histological images. The color scale of these images can be adjusted to contrast features to aid in diagnosis. FIGS. 14C and 14D show a pseudo color and histology images of breast tissue sarcoma. FIGS. 14E and 14F show pseudo color and histology images of tissue with metastatic brain cancer.

Figure 14G:
FIG. 14G is a reflectance image acquired at 402 nm that mimics cytoplasmic stains.
Figure 14H:
FIG. 14H is an autofluorescence image mimicking cytoplasmic staining.
Figure 14I:
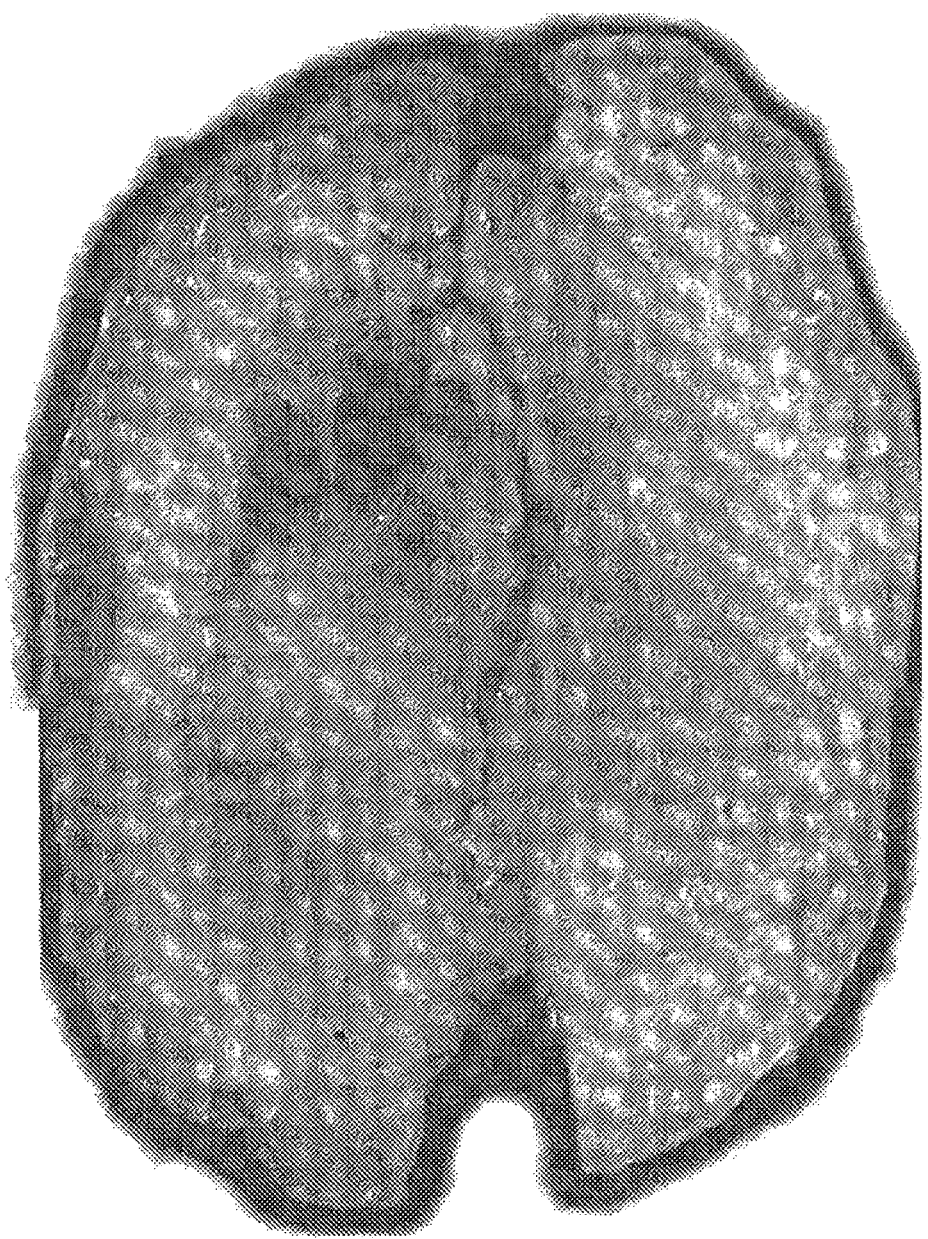
FIG. 14I is a fluorescence image of tetracycline in tissue.

Shown in FIG. 14G is a reflectance image of tissue obtained at 402 nm that can be used to mimic a cytoplasmic stain. Thus certain imaging modalities can be employed instead of stains that provide sufficient contrast to assist in diagnostic image analysis. Shown in FIG. 14H is an autofluorescence image of the same sample that was illuminated with 402 nm light. The image was obtained with autofluorescence light in the range of 411-421 nm. Note that the excitation wavelength can be shifted to alter the detected autofluorescence spectral band. The filtering system can also be adjusted to shift the detected spectral band. Shown in FIG. 14I is the tissue sample stained with tetracycline to obtain a fluorescence image collected in the 530-590 nm range based on 402 nm excitation. The emission band can be selected in the range between 405 nm and 620 nm and the image co-registered with an autofluorescence image or with images using other stains.

Figure 14J:
FIG. 14J is an H&E histopathology imaging showing the staining pattern of the sample shown in FIGS. 14G-14I.

Shown in FIG. 14J is a hematoxylin and eosin stain image of the sample shown in FIGS. 14G-14I.

Figure 15A:
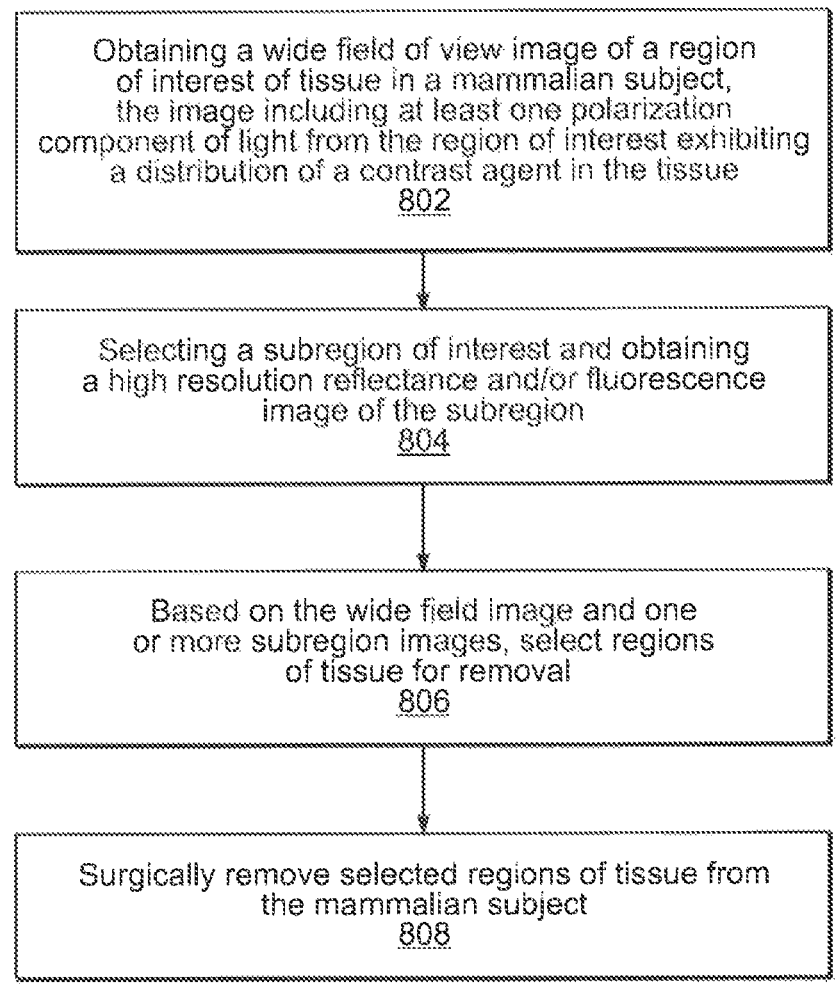
FIGS. 15A and 15B show process sequences in accordance with preferred embodiments of the invention.

A preferred method of performing wide field imaging in combination with high resolution fluorescence imaging is shown in FIG. 15A. The surgical procedures described previously herein further can include a method 800 in which a wide field of view image is first obtained 802 of a region of interest to evaluate a surgical margin during surgery. Based on the first image and the distribution of a contract agent displayed therein, one or more sub-regions can be selected 804 for high resolution imaging. The high resolution images can provide cellular level analysis of selected regions. Based on review of the imaged sub-region, additional sections of tissue can be removed 806 from the surgical site.

Figure 15B:
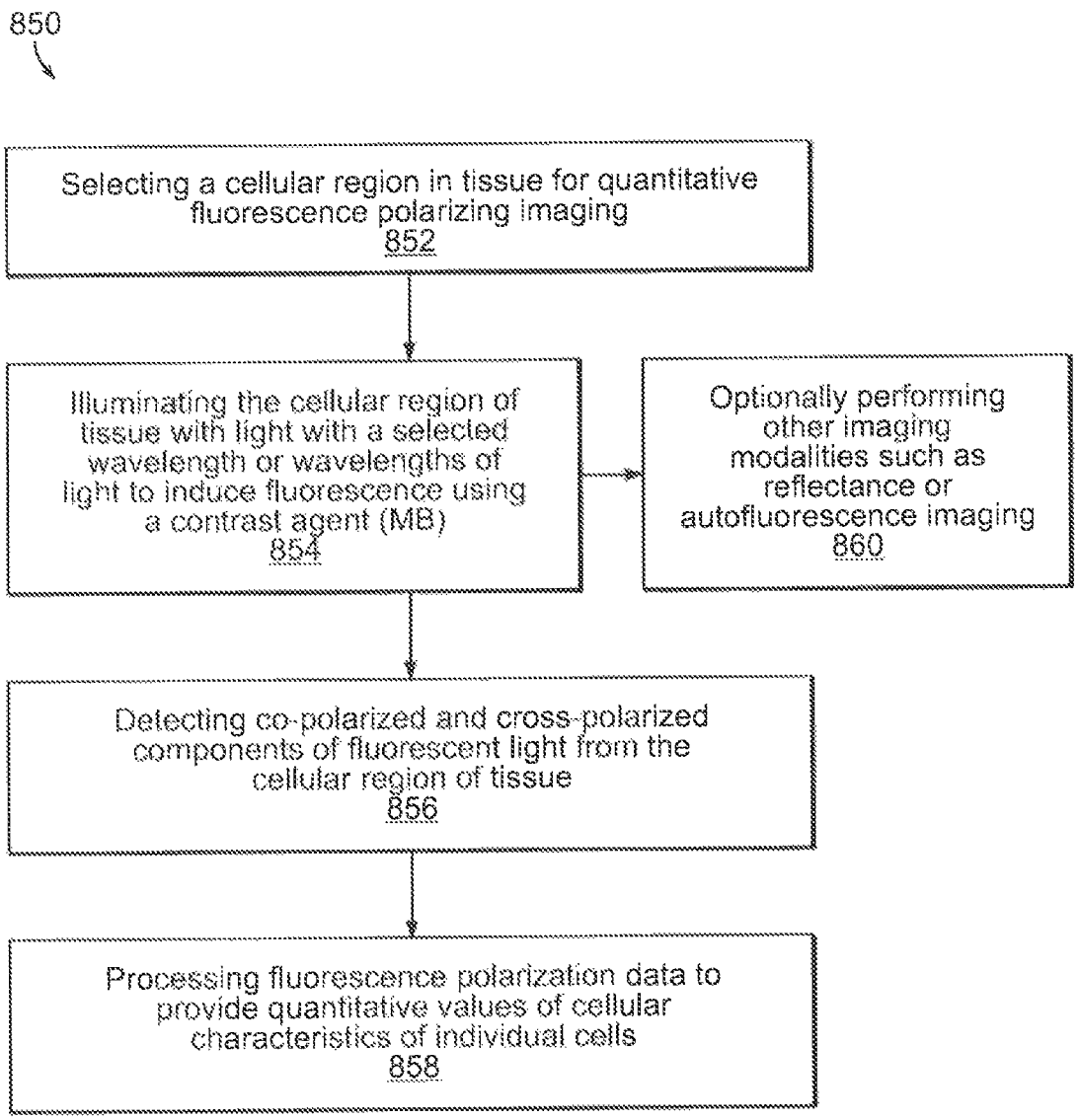

Shown in FIG. 15B is another preferred method 850 in accordance with the invention for cellular imaging. After selecting 852 a region of tissue, different imaging modalities can be selected using the confocal imaging system as described herein. The sample can be prepared with a stain, such as methylene blue, and the sample can be illuminated 854 with light of a wavelength to induce fluorescence. Alternatively, other images such as autofluorescence or reflectance images can be obtained 860 for use in subsequent analysis. The co-polarized and cross-polarized fluorescence components can be detected 856 and the results analyzed 858 to provide quantitative values of cellular characteristics of cells within the region.

While the present invention has been described here in conjunction with certain preferred embodiments, a person with ordinary skill in the art, after reading the foregoing specification, can effect changes, substitutions of equivalents and other alterations to the systems and methods described herein. Each embodiment described above can also have included or incorporated therewith such variation as disclosed in regard to any and all of the other embodiments. Thus, it is intended that the scope of the claims granted herewith be limited in breadth only by definition as defined in the specification and appended claims and any equivalents thereof.

What is claimed is:

1. A method for evaluating tissue for cancer on a cellular level, the method comprising the steps of:
    illuminating a region of tissue with a first wavelength of light;
    generating an image of the region of tissue based on light emitted from the region in response to the illumination of the region by the first wavelength of light;
    selecting at least one sub-region in the region based on the image generated from the first wavelength of light;
    imaging a confocal point of a second wavelength of linearly-polarized light onto the sub-region;
    scanning the confocal point of the second wavelength of light through the sub-region;
    focusing fluorescence light emitted from the scanned confocal point that is scanned through the sub-region onto a pinhole;
    detecting, with a confocal imaging system, after it has passed through the pinhole, co-polarized and cross-polarized fluorescence light emitted from the scanned confocal point that is scanned through the sub-region;
    generating a fluorescence polarization image of the sub-region based on the detected co-polarized and cross-polarized light, the fluorescence polarization image including a resolved image of a cell in the sub-region, wherein the generating includes determining, based on co-polarization and cross-polarization image values of pixels of the resolved image of the cell, an exogenous fluorescence polarization value for the cell, wherein the exogenous fluorescence polarization value indicates an intrinsic fluorescence polarization of the cell; and
    displaying the fluorescence polarization image, wherein the displayed image visually indicates, based on the exogenous fluorescence polarization value for the cell, whether the cell is cancerous or non-cancerous.

2. A method as recited in claim 1, wherein the first and second wavelength of light are different.

3. A method as recited in claim 1, wherein the second wavelength of light is in a range of 370 to 670 nm.

4. A method as recited in claim 1, further comprising the step of applying a first contrast agent to the region, the first contrast agent having a fluorescent response to the first wavelength of light.

5. A method as recited in claim 1, further comprising generating a confocal reflectance image of the sub-region based on the light detected in response to the scanned confocal point of the second wavelength of light.

6. A method as recited in claim 5, further comprising displaying the confocal reflectance image along with the fluorescence polarization image in a fused pseudo-color image.

7. A method as recited in claim 1, further comprising the step of detecting and presenting a wide-field fluorescence polarization image from the first wavelength of light for grossly visually delineating a tumor in the region during surgery.

8. A method as recited in claim 1, further comprising the steps of: applying a first contrast agent to the region as a cytoplasmic stain; and applying a second contrast agent to the region as a nuclear stain.

9. A method as recited in claim 1, further comprising the step of determining whether or not additional tissue should be removed from the at least one sub-region during surgery.

10. A method as recited in claim 1, wherein the indication of whether the cell is cancerous or non-cancerous is based, at least in part, on the fluorescence polarization value associated with the cell.

11. A method as recited in claim 1, wherein the fluorescence polarization image of the sub-region is based on quantitative fluorescence polarization values for pixels of the image.

12. A method as recited in claim 1, further comprising confirming whether the cell is cancerous or non-cancerous is based, at least in part, on the fluorescence polarization value associated with the cell.

13. A method as recited in claim 6, wherein a color scale of the pseudo-color image is selected to contrast cancerous cells from non-cancerous cells.

* * * * *